United States Patent [19]
Dressman et al.

[11] Patent Number: 5,789,393
[45] Date of Patent: Aug. 4, 1998

[54] PHARMACEUTICAL COMPOSITIONS AND USES OF WATER-SOLUBLE, HIGH-VISCOSITY GRADE CELLULOSE ETHERS

[75] Inventors: Jennifer B. Dressman, Paris, France; Christos Reppas, Athens, Greece; Stephen W. Tobey, Midland, Mich.; Cynthia W. Sowle, Carmel, Ind.

[73] Assignees: The Board of Regents of the University of Michigan, Ann Arbor; The Dow Chemical Company, Midland, both of Mich.

[21] Appl. No.: 477,371

[22] Filed: Jun. 7, 1995

Related U.S. Application Data

[63] Continuation of Ser. No. 353,949, Dec. 9, 1994, Pat. No. 5,576,306, which is a continuation of Ser. No. 62,697, May 17, 1993, abandoned, which is a continuation of Ser. No. 870,601, Feb. 21, 1992, abandoned, which is a continuation-in-part of Ser. No. 663,381, Mar. 1, 1991, abandoned.

[51] Int. Cl.$^6$ .......... A61K 31/715; C08B 11/02; C08B 11/00; C07H 15/04
[52] U.S. Cl. .......... 514/57; 536/56; 536/84; 536/120
[58] Field of Search .......... 514/57; 536/56, 536/84, 120

[56] References Cited

U.S. PATENT DOCUMENTS

| | | | |
|---|---|---|---|
| 3,617,588 | 11/1971 | Langman | 264/486 |
| 4,820,813 | 4/1989 | Schulz | 536/84 |
| 5,281,584 | 1/1994 | Tobey | 514/57 |

*Primary Examiner*—John Kight
*Assistant Examiner*—Everett White
*Attorney, Agent, or Firm*—Rohm & Monsanto

[57] ABSTRACT

Water-soluble, high-viscosity grade cellulose ether compositions are useful for the reduction of serum lipid levels, particularly total serum cholesterol, serum triglycerides, and low-density lipoprotein (LDL) levels and/or attenuate the postprandial rise of blood glucose levels in animals. The pharmaceutical uses of compositions for reducing cholesterol levels additionally include the treatment of diabetes and/or hypercholesterolemia, with avoidance of many of the undesirable side effects associated with other forms of treatment. The composition may be in the form of a prehydrated ingestible composition, such as a gelatin, or a comestible, such as a cookie. In addition, the compositions of the present invention are palatable to the patient, thereby enhancing patient compliance with the regimen.

13 Claims, 5 Drawing Sheets

PHARMACEUTICAL COMPOSITIONS AND USES OF WATER-SOLUBLE, HIGH-VISCOSITY GRADE CELLULOSE ETHERS

This is a continuation of application Ser. No. 08/353,949, U.S. Pat. No. 5,576,306 filed Dec. 9, 1994 as a continuation of Ser. No. 08/062,697 filed May 17, 1993, now abandoned, as a continuation of Ser. No. 07/870,601 filed Feb. 21, 1992, now abandoned, which was a continuation-in-part of Ser. No. 07/663,381 filed Mar. 1, 1991, now abandoned.

BACKGROUND OF THE INVENTION

This invention relates generally to pharmaceutical uses of compositions of water-soluble high-viscosity grade cellulose ethers, and more particularly, to compositions which contain water-soluble, high-viscosity grade cellulose ethers for effecting reduction in serum lipid levels, particularly total serum cholesterol, serum triglycerides, and LDL cholesterol levels, and/or for attenuating postprandial rise of blood glucose levels.

Diabetes

Diabetes mellitus is a disease which affects nearly 15 million people in the United States and, although a heterogenous disorder, it generally is classified within two major categories, i.e., Type I and Type II. The term "juvenile-onset" diabetes has been replaced by "insulin-dependent diabetes" (IDDM), or Type I diabetes. This type of diabetes may occur at any age, and is characterized by insulin deficiency, dependence on insulin, proneness to ketosis, and by an abrupt onset in most cases. In adults, however, the onset tends to be more indolent with better preservation of β-cell function. Both genetic and environmental factors (e.g., viruses) triggering an autoimmune disorder are considered important in its development. About 15 percent of the diabetics in the USA are Type I diabetics.

The term "maturity-onset" diabetes has been replaced by "non-insulin dependent" diabetes (NIDDM), or Type II diabetes. About 80% of all diabetics in the United States are in this category. This type of diabetes is characterized by both impaired insulin secretion and insulin resistance. The majority of patients are obese adults and loss of weight can restore normoglycemia in some cases. However, this type of diabetes can also occur in the non-obese and in children. They are not insulin dependent or ketosis prone, although insulin may be used if diet and oral hypoglycemic agents fail to provide adequate treatment. There is a strong genetic basis for this type of diabetes but no evidence for an autoimmune disorder.

A few patients, perhaps 5 percent of those who appear to have NIDDM, may actually have a slowly progressive form of IDDM, as evidenced by the presence of islet-cell antibodies. These patients eventually become dependent on insulin.

The generally accepted aims in the treatment of diabetes are to provide:

a. Relief from symptoms;

b. Improvement of the quality of life; and c. Prevention of both acute (e.g., hyperosmolar coma and ketoacidosis) and chronic complications (e.g., neuropathy, nephropathy and premature atherosclerosis).

Insulin administration is the treatment of choice in IDDM diabetics and in some NIDDM cases. The recent introduction of human insulin, with subsequent reduction in the cost, and advances in formulation has made this method of treatment more efficient. Additionally, human insulin is the treatment of choice for those diabetics with rare conditions such as anti-insulin antibodies, insulin resistance and insulin allergies. In general, patients treated with human insulin have lower rates of anti-insulin antibodies than those treated with porcine preparations, but the significance of these lower levels is unclear. Nevertheless, there are major problems associated with this type of treatment, including the possibility of allergic reactions, complicated dosing regimens, and above all episodes of severe hypoglycemia. All too often, such episodes are severe enough to require the assistance of another person, and sometimes result in coma. A frequent complication of intensive insulin therapy is nocturnal hypoglycemia with a nadir in blood glucose levels between 2 a.m. and 3 a.m.

Treatment with oral hypoglycemic agents is usually prescribed in NIDDM diabetics. Since insulin resistance and impaired secretion are key factors in the pathogenesis of NIDDM, treatment is directed toward restoring metabolic normality by improving insulin secretion and reducing insulin resistance. Since insulin resistance is tied with increased body weight, the initial approach involves a program of diet and exercise. Failure of such therapy triggers the initiation of pharmacologic treatment. To date the most effective oral hypoglycemic agents include sulfonylureas and biguanides as well as some other drugs which are currently undergoing clinical investigation.

In the United States there are several sulfonylureas currently available, including tolbutamide, acetohexamide, tolazamide, chlorpropamide, glipizide and glyburide. Their mechanism of action basically lies in their ability to increase β-cell sensitivity to glucose. Therefore, they are ineffective in patients with IDDM who lack islet, β-cells, and in those who have undergone pancreatectomy. During the 1970's, a controversial study indicated that tolbutamide lacks efficacy and is associated with an increase risk of cardiovascular mortality. In the late 1970's the use of sulfonylureas was revived, and as a result, both the number and the percentage of patients whose diabetes is treated with sulfonylureas are increasing. Nearly 40% of those with NIDDM in the United States are now treated with these drugs.

Sulfonylureas are generally well tolerated drugs and only 2% of patients discontinue therapy because of side effects. The most important side effects are GI disturbances and weight gain. As for all the pharmacologic hypoglycemic agents, the most common severe complication is hypoglycemia. In a prevalence survey conducted in Britain, 20% of the patients treated with sulfonylureas had at least one episode of symptomatic hypoglycemia within a six-month period. However, data from Sweden and Switzerland indicate that the incidence of severe hypoglycemia due to sulfonylureas is about 0.22 per 1,000 patient-years as compared with an incidence of about 100 per 1,000 patient-years for insulin. Another problem with sulfonylurea drugs are that they cross the placenta and stimulate the release of insulin from fetal β-cells. In addition, other drugs may influence the hypoglycemic actions of sulfonylureas through pharmacodynamic and pharmacokinetic interactions. Therefore, these drugs should be given cautiously and in reduced doses to patients with liver disease or who are taking other medications. Finally, the sulfonylureas are contraindicated in patients allergic to sulfa drugs and in patients with IDDM, since they are ineffective in the absence of endogenous insulin.

No biguanides are currently used in the United States. Only the biguanide metformin, which is widely used in Europe and Canada, and which accounts for the 25% of the prescriptions for oral hypoglycemic agents world-wide, is now undergoing clinical trials in the United States. Compared to the sulfonylureas, metformin rarely causes hypoglycemia or weight gain, yet provides much better control of the blood lipid levels. The mechanism of action of metformin is not clearly understood. The mechanism does not, however, involve the stimulation of insulin secretion. Reduced gastrointestinal (GI) absorption of glucose, stimulation of anaerobic glycolysis, inhibition of gluconeogenesis, stimulation of tissue glucose uptake and increased insulin-receptor binding have all been proposed as modes of action. Metformin appears to be slightly less well tolerated than sulfonylureas since almost 5% of patients have side effects that lead to the withdrawal of the drug. The most common side effects are gastrointestinal and occur initially in 5–20% of patients, but these effects are usually transient. A rare but serious side effect is lactic acidosis, which has been fatal in 30% of patients in whom it develops. Finally, metformin's use is contraindicated in patients with renal insufficiency, in those who are pregnant, and in those whose tissue anoxia and altered cellular metabolism may promote the production of lactate.

Hypercholesterolemia

Lipids are transported in the blood by the plasma lipoproteins. Lipoproteins (which account for 8% to 10% of the total serum protein) contain specific proteins (known as apolipoproteins), and varying amounts of cholesterol, triglycerides and phospholipids. The three major classes of lipoproteins found in the plasma in the fasting state are very low density lipoproteins (VLDL), low density lipoproteins (LDL) and high density lipoproteins (HDL). VLDLs contain over 50% triglyceride, about 20% cholesterol and about 10% protein. LDLs are much smaller particles and contain about 50% cholesterol, 20% protein and about 5% triglyceride. HDLs are the smallest of the lipoproteins and contain about 50% protein, 10% triglyceride and 20% cholesterol. In addition, chylomicrons, which are synthesized in the intestine in response to a fat-containing meal, appear transiently in the plasma and are cleared from the circulation within a few hours. They are not normally present in the fasting state, and contain about 90% by weight triglycerides, and 5% cholesterol.

In the normal adult human, LDLs carry about 65% of the circulating cholesterol, HDLs carry about 25% and VLDLs carry about 10%. In order to estimate individual cholesterol concentrations, total cholesterol, triglycerides and HDL cholesterol are measured, and LDL cholesterol is calculated from a known empirical relationship:

*LDL cholesterol=Total cholesterol−HDL cholesterol−(Triglycerides/5)* where the concentrations are expressed in mg/dL. The expression, "triglycerides/5," is an estimate of VLDL cholesterol concentration and is based on the ratio of cholesterol:triglyceride in VLDL.

It has recently been reported that use of the ratio "triglyceride/6.3" gives a more nearly accurate measure of VLDL cholesterol. Also, this relationship is valid only if the triglyceride levels are less than 800 mg/dL. Otherwise, LDL cholesterol level should be measured directly.

High blood cholesterol levels are believed to be responsible in many cases for the development of atherosclerosis in humans. The drugs of first choice in the treatment of hypercholesterolemia (high blood cholesterol levels) are bile acid sequestrants (e.g., cholestyramine, colestipol) and nicotinic acid. Nicotinic acid (niacin) lowers lipids by decreasing the synthesis of VLDL particles from the liver, which, in turn, suppresses the formation of LDL cholesterol. Vasodilation is a major side effect of niacin. This causes an intense feeling of warmth, flushing, headache, and lightheadedness. Cholestyramine has been shown to lower CHD risk in clinical trials, and its long-term safety has been established. However, this drug requires considerable patient education to achieve adequate compliance.

Cholestyramine and colestipol are nonabsorbable anion exchange resins that bind bile acids in the intestinal lumen. As a consequence, they increase the conversion of cholesterol to bile acids in hepatic cells and stimulate the synthesis of LDL receptors on cell walls. The increase in LDL receptor number increases the uptake from the plasma into cells, leading to a reduction in total cholesterol in the blood. These agents are capable of significantly reducing blood cholesterol. In fact, resin therapy has been shown to be significantly effective in reducing mortality and morbidity. The magnitude of the reduction in lipids achieved with bile acid sequestrants is a function of the dose administered. In one study, each packet of cholestyramine administered decreased total cholesterol approximately 3%. Thus, 2 to 4 packets per day (8 to 12 g of cholestyramine) should reduce total cholesterol about 10%, while a full dose of 5 to 6 packs per day (20–24 g) should reduce total cholesterol 16%.

Cholestyramine, which has a gritty texture, is an astringent and unpleasant to swallow when consumed orally. Another difficulty in using bile acid sequestrants is the frequency of side effects associated with their use. Bloating, fullness, abdominal pain, constipation, flatulence, nausea and other gastrointestinal complaints occur in approximately 70% of patients taking these agents and this deters compliance with therapy. In some studies, reductions in total cholesterol had dropped from 14% to 10% while those for LDL cholesterol had dropped from 20% to 15%, most likely because of poor compliance with therapy.

Also, cholestyramine has the side effect of binding with other drugs and therapeutic agents, thereby reducing their availability. To minimize this interaction (i.e., reduced absorption of drugs due to absorption on the resin), drug administration should be done at least one hour before, or four hours after, the resin.

Processes for preparing compositions which include cholestyramine are known, such as those described in U.S. Pat. Nos. 3,308,020; 3,383,281; 3,499,960; and 3,947,272. The maximal effective daily dose is 24 g for cholestyramine and 30 g for colestipol.

Role of Fiber in Treatment of Diabetes and Hypercholesterolemia

Many investigators have studied the effects of dietary fiber in controlling diabetes. The relationship between dietary fiber, diet content and carbohydrate and lipid metabolism appears to be rather complex. For dietary fiber to exert its optimum effect, it may have to be given as a part of a high-carbohydrate diet. Fiber added to a low-carbohydrate diet of diabetic patients appears to have little effect. By contrast, when the same fiber is added to high-carbohydrate diets, consistent improvements are seen.

On the other hand, the addition of certain soluble fibers to meals, such as guar, pectin, etc., will yield reduced postprandial glycemia in both normal and diabetic subjects. In diabetics, this reduction may be sufficient to permit a reduction in the required dose of insulin. It is thought that supplemental fibers can be effective only if they can form viscous solutions in water. Non-viscous guar, for example, has no effect on postprandial glucose levels. However, not all water-soluble fibers are efficacious. Gum tragacanth, for example, lacks the ability to attenuate glucose levels except for a transient effect at the start of the postprandial period.

Ingested soluble vegetable fibers such as psyllium, guar, and β-glucans may also exert cholesterol lowering effects, but these soluble fibers are not very efficacious on a per gram basis. Also, since soluble vegetable fibers are easily metabolized by colonic bacteria (causing extensive anaerobic production of methane, carbon dioxide, and hydrogen), these vegetable fibers are well known to cause gross flatulence, bloating, and extreme abdominal discomfort when administered in therapeutically effective doses. It is to be noted that psyllium is prepared from its seed husk which is typically contaminated with proteinaceous hull which carries certain allergens known to be associated with psyllium.

Ground psyllium seed is recognized for its ability to lower serum cholesterol levels and to attenuate excess blood glucose levels, also known as hyperglycemia, in human patients. EPO Published Patent Application 0362926, published on Apr. 11, 1990, describes the use of products containing psyllium seed husk to be effective in reducing human serum cholesterol levels and in controlling blood glucose levels in diabetics.

EPO Published Patent Application 0309029, published on Mar. 29, 1989, describes cookies containing psyllium and polyol polyesters which are useful in reducing blood cholesterol levels.

EPO Published Patent Application 0323666, published on Jul. 12, 1989, describes the use of products containing cholestyramine in combination with psyllium or with polyol polyesters as orally administered cholesterol-lowering compositions.

The reduction of total serum cholesterol by psyllium appears to be mediated through a lowering of LDL cholesterol. Reduction of triglyceride levels is not as consistent. Studies have not shown any effect of guar on triglyceride levels.

One study conducted on psyllium has shown this material to reduce total serum cholesterol by 15%. However, additional clinical studies have shown that the usual reduction was more commonly in the 4-6% range. Other fibers, such as wheat bran, cellulose, and lignin, are ineffective to control serum cholesterol. Such additional studies also failed to find any reduction of cholesterol levels during treatment with pectin.

It has been established that the unpalatability of compositions currently being marketed to treat hypercholesterolemia or hyperglycemia is a primary factor causing the low rate of compliance by human patients to adhere to diets requiring daily consumption of these compositions. For both oat bran and guar, several gastrointestinal side effects, such as flatulence, diarrhea, abdominal cramps, etc., lead to very poor patient compliance. Additionally, long-term administration of fiber may cause vitamin and mineral depletion. The low compliance rate indicates a definite need for a hypocholesteremia- and/or hyperglycemia-controlling composition which is both more palatable and more effective than the known compositions.

There is, therefore, a need for a system which achieves selective reduction of LDL serum cholesterol levels and the attenuation of the postprandial rise of blood glucose levels in an animal by the use of pharmaceutical compositions containing water-soluble, high-viscosity grade cellulose ethers. There is additionally a need for a system which solves the above-described problems by either reducing serum cholesterol levels and/or attenuating the postprandial rise of blood glucose levels in an animal, particularly human patients, with the use of compositions which are more palatable and more effective than the known compositions.

It is, therefore, an object of this invention to provide a dietary supplement which significantly lowers postprandial blood glucose response levels and/or serum lipid levels.

It is another object of this invention to provide a dietary supplement which significantly lowers total serum cholesterol, LDL cholesterol and triglyceride levels, without significantly affecting HDL cholesterol levels.

It is also another object of this invention to provide a dietary supplement which significantly lowers postprandial blood glucose response levels and/or serum lipid levels while advantageously having but a minimal, if any, effect on the assimilation of micronutrients.

It is also an object of this invention to provide a dietary supplement which significantly and consistently lowers serum cholesterol levels in >95% of all subjects tested.

It is a further object of this invention to provide a dietary supplement which significantly lowers postprandial blood glucose response levels and/or serum lipid levels and which is well-tolerated by test subjects in the dosage range required for consistent efficacy.

It is additionally an object of this invention to provide a dietary supplement which significantly lowers postprandial blood glucose response levels and/or serum lipid levels while minimizing adverse side effects such as abdominal discomfort, flatulence, diarrhea, and the like, caused by dietary fibers in the prior art.

It is yet a further object of this invention to provide a dietary supplement which significantly lowers postprandial blood glucose response and/or serum lipid levels without systemic side effects.

It is also another object of this invention to provide a dietary supplement which is not fermentable and therefore has less potential for producing gas in the colon.

It is yet an additional object of this invention to provide a composition for lowering postprandial blood glucose response and/or serum lipid levels which has a dosage which can be accurately defined.

It is still another object of this invention to provide a dietary supplement which can be stored at room temperature.

It is a yet further object of this invention to provide a dietary supplement which significantly lowers postprandial blood glucose response levels and/or serum lipid levels and which is well-tolerated by test subjects without risk of allergic reaction.

SUMMARY OF THE INVENTION

The foregoing and other advantages are achieved by this invention which provides in a first composition aspect thereof, an ingestible composition for effecting reduction of serum lipid levels and/or attenuation of postprandial rise of blood glucose levels in an animal. In accordance with the invention, the composition provides a total of at least 5 grams, and up to about 50 grams, per day of a water-soluble, high-viscosity grade cellulose ether, and at least one pharmaceutically-acceptable inert ingredient.

As used herein, the term "pharmaceutically acceptable inert ingredient" is meant to represent an edible, non-toxic material which may be mixed with the water-soluble, high-viscosity cellulose ethers of this invention in a composition useful for reducing serum lipid levels and/or for attenuating postprandial rise of blood glucose when administered to an animal. Typically, such a pharmaceutically acceptable inert ingredient will be in a liquid or a solid form and may be an edible food matrix such as described herein.

In one embodiment of the invention, the ingestible composition is further provided with water in an amount sufficient to hydrate, dissolve, and disperse the high-viscosity grade cellulose ether.

One significant characteristic of the high-viscosity grade cellulose ether is that it is non-toxic, non-ionic, inert, and, of course, edible. Some of the high-viscosity grade cellulose ethers, in the various embodiments, belong to the chemical categories hydroxypropylmethylcellulose, methylcellulose, or hydroxyethylcellulose.

In a particular ingestible composition embodiment of the invention, in the form of an aqueous gelatin composition, the ingestible composition contains, by weight percent:

a. approximately between about 60% and about 99% of water;

b. approximately between about 0.5% and about 10% of gelatin; and c. approximately between about 0.5% and about 5.0% high-viscosity grade cellulose ether.

In a comestible composition aspect of the invention, illustratively in the form of a cookie formulation, the comestible composition is provided with:

a. approximately between about 10% and about 25% of water-soluble, high-viscosity grade cellulose ether;

b. approximately between about 10% and about 40% of all-purpose flour;

c. approximately between about 5% and about 30% sweetener;

d. approximately between about 5% and about 40% of water; and e. the remainder being in the form of conventional cookie additives.

In accordance with a method of selectably effecting reduction of serum lipid levels and/or effecting attenuation of the postprandial rise of blood glucose levels in a person or animal needing such treatment, the method includes the step of administering to the person or animal a composition having a water-soluble, high-viscosity grade cellulose ether in an amount effective to achieve the desired effect on the person or animal.

Typically the amount of high-viscosity grade cellulose ether which is employed is at least 10 grams. In most embodiments, the amount of high-viscosity grade cellulose ether is between 10 and approximately 50 grams on a per diem basis. With respect to reduction of low-density lipoprotein serum cholesterol, the amount of high-viscosity grade cellulose ether which is administered is in an amount effective to achieve a post-treatment level of low-density lipoprotein serum cholesterol in the animal which is at least 15 percent lower than the pre-treatment level. Of course, the high-viscosity grade cellulose ether can be used in an amount effective to achieve a desired level of control over the postprandial rise in the blood glucose in the patient, preferably during, or concomitant with, a meal.

As previously noted, the present invention is directed to the selective reduction of low-density lipoprotein (LDL) serum cholesterol levels and/or the attenuation of the postprandial rise of blood glucose levels in an animal, particularly humans. The compositions administered to a patient in need of such treatment are suitable for oral ingestion and contain as the active ingredient a water-soluble, high-viscosity grade cellulose ether. Accordingly, the cellulose ether should be non-toxic to the animal or human patient, and is preferably non-ionic, inert such that it is resistant to attack by enzymes or bacteria in the gastrointestinal tract. As indicated, the edible composition of the invention is without a poor or bad taste.

BRIEF DESCRIPTION OF THE DRAWINGS

These and other objects, features, and advantages of the invention will be better appreciated from consideration of the following detailed description read in conjunction with the accompanying drawings, wherein.

DETAILED DESCRIPTION

Figure 1:
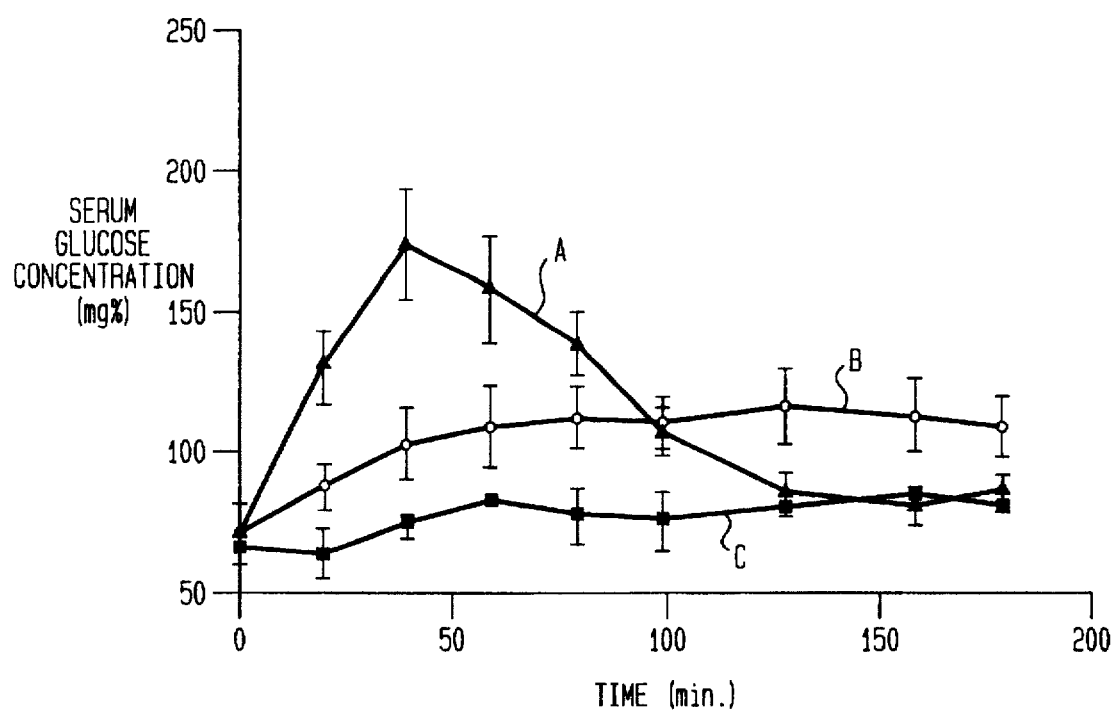
FIG. 1 is a graphical representation of serum glucose concentration level vs. time curves in dogs following, in one curve ("B"), coadministration of a water-soluble high-viscosity cellulose ether, specifically a hydroxypropylmethylcellulose in 1:20 aqueous glucose solutions, in accordance with the present invention.

Cellulose ethers have long been used in many industries as, for example, viscosity control agents, emulsifiers, and binding agents. The use of cellulose ethers in pharmaceutical products is also well known. The usual function of cellulose ethers in pharmaceutical products is to serve as a coating, compounding aid, or controlled release agent. Typically, only minimal quantities, meaning either representing only a small percentage of a formulation or providing only a few tenths of a gram per daily dose, of the cellulose ether are required for such uses. Cellulose ethers have been used in certain bulk laxative products in which a low-viscosity grade of a water-soluble methylcellulose comprises the active pharmaceutical ingredient. The recommended dosage for this bulk laxative product is 2 to 6 grams of the cellulose ether per day.

The cellulose ethers which are useful in the present invention are those which reduce the serum lipid levels and/or attenuate the postprandial rise in the blood glucose level in an animal. These particular cellulose ethers unexpectedly help to selectively reduce an animal's serum lipid levels, specifically total serum cholesterol, triglycerides, and LDL levels; or to better control the animal's postprandial rise in blood glucose level when compared to the performance of other known products.

The cellulose ethers used in the present invention may be prepared by any of a number of known processes. Illustrative processes are set forth in U.S. Pat. Nos. 3,342,805; 3,388,082; 3,709,876; 4,477,657; 4,410,693; and 4,820,813, the disclosures of which are hereby incorporated by reference. Generally, a specific cellulose ether is prepared by the formation of an alkali cellulose by the addition of sodium hydroxide to a slurry of cellulose floc in a diluent. The alkali cellulose is then reacted with an appropriate alkylating agent or agents, under pressure. Thereafter, the slurry is neutralized and the product is extracted, dried, and ground.

The particular water-soluble cellulose ethers which are useful in the present invention are those which are of a high-viscosity grade. By "high-viscosity grade" is meant those cellulose ethers that, when in a 2 weight percent aqueous solution, exhibit a viscosity at 20° C. of greater than about 10,000 centipoise (cP) (10,000 mPa·s) and may have a viscosity as high as 2,000,000 cP (2,000,000 mPa·s). Such viscosities may generally be measured by conventional methods, for example, by measuring the viscosity of an aqueous solution of the polymers at the desired concentration in Ubbelohde capillary tubes at the specified temperature. Preferably, the cellulose ethers, when in a 2 weight percent aqueous solution at 20° C., exhibit a viscosity ranging from about 25,000 cP (25,000 mPa·s) to about 800,000 cP (800,000 mPa·s). Most preferably, the cellulose ethers, when in a 2 weight percent aqueous solution at 20° C., exhibit a viscosity ranging from about 50,000 cP to about 600,000 cP. Conversely, by "low-viscosity grade" is meant those cellulose ethers that, when in a 2 weight percent aqueous solution, exhibit a viscosity at 20° C. below about 10,000 cP (10,000 mPa·s).

"High-molecular weight" for methylcellulose (MC) and hydroxypropylmethylcellulose (HPMC) ethers refers to those MC and HPMC ethers having a number-average molecular weight which is greater than about 1,000,000 daltons, and preferably from 100,000 to 250,000 daltons. These high molecular weight MC and HPMC ethers are also characterized as "high-viscosity," which means that when they are present in a 2 weight percent aqueous solution, they exhibit a viscosity at 20° C. greater than about 10,000 cP (10,000 mPa·s), and preferably from about 25,000 cP (25,000 mPa·s) to 2,000,000 cP (2,000,000 mPa·s).

In certain advantageous embodiments of the invention, water-soluble, high viscosity cellulose ethers having a viscosity greater than about 100,000 cP (100,000 mPa·s) as a 2 weight percent aqueous solution at 20° C. may be prepared, for example, by a process taught in U.S. Pat. No. 4,820,813 wherein a substantially dry high molecular weight cellulose ether is ground under conditions of mild mechanical impact such as those encountered in a high speed air swept impact mill.

The cellulose ethers employed in the present invention must be water-soluble. As used herein, the term "water-soluble" means that two grams of a powdered cellulose ether of the present invention can be dispersed by stirring into 100 grams of water at a temperature between about 0° C. and 100° C., to provide a substantially clear solution or dispersion (gel) when the dispersion is brought to a temperature of 20° C.

Examples of cellulose ethers which are useful in the present invention include such known cellulose ethers as methylcellulose, methylethylcellulose, hydroxypropylmethylcellulose, hydroxypropyl cellulose, and hydroxy-ethyl methylcellulose. Mixtures of such known cellulose ethers may also be used in the present invention. The most preferred cellulose ether for use in the present invention is the semisynthetic polymer, hydroxypropylmethylcellulose.

Descriptions of suitable cellulose ethers, which meet the criteria of the present invention as described herein, can be found in the following references: alkyl and hydroxyalkylalkylcellulose (Chapter 3), hydroxy-ethyl-cellulose (Chapter 12), and hydroxypropylcellulose (Chapter 13) in Handbook of Water-Soluble Gums and Resins, ed. R. L. Davidson, pub. McGraw-Hill (1980); and hydroxypropylmethylcellulose (pp 670–71) and methylcellulose (pp 864–865) in The United States Pharmacopeia, (The National Formulary), (USP XXII, 1990). The disclosures of these reference sources are hereby incorporated by reference.

Examples of suitable cellulose ethers of the present invention include those which may be obtained commercially, such as METHOCEL™ (available from The Dow Chemical Company, Midland, Mich., USA) and METOLOSE™ or PHARMACOAT™ (available from the Shin-etsu Chemical Company, Tokyo, Japan). The METHOCEL™ cellulose ethers, for example, are particularly advantageous because they can be obtained in a wide variety of molecular weights, substitution patterns, and viscosity characteristics. In particular, hydroxypropylmethylcelluloses sold as the METHOCEL™ K series, and certain polymers and polymer combinations within the METHOCEL™ E, F, and J series, are particularly suitable. Certain higher molecular weight methylcellulose polymers within the METHOCEL™ A series are also suitable.

The high-viscosity grade, water-soluble cellulose ethers of the present invention are inert, non-ionic cellulose ethers which are known to be edible. The use of such high-viscosity grade cellulose ethers in an edible composition is characterized in that the high-viscosity grade cellulose ethers: 1) are resistant to bacterial fermentation in the large bowel of the animal and, therefore, avoid gas production resulting from such fermentation, 2) are substantially inert to attack by enzymes found in the digestive tract, 3) do not produce the allergic responses characteristic of many known vegetable fibers, and 4) interfere minimally with micronutrient absorption.

The high-viscosity grade cellulose ethers of the present invention are further characterized in that they are generally palatable to animals and/or can be easily incorporated into a composition which can be made to be palatably acceptable to an animal, particularly a human patient.

For the purposes of the present invention, the term "animal" means a warm-blooded mammal, especially a human.

As will become evident from the discussion herein relating to investigative studies of the effects of administering exemplary cellulose ethers to an animal, a characteristic of the cellulose ethers within the contemplation of the invention is the ability of these cellulose ethers to increase the lumenal viscosity of the gastrointestinal tract to at least a consistency index value (K) of about K=10,000 at 37° C. The consistency index is a dimensionless constant derived from the overall viscosity/shear profile (range 100 sec$^{-1}$ to 1000 sec$^{-1}$) and is proportional to viscosity. The maximum consistency index for administered cellulose ethers is about K=200,000. Use of cellulose ethers having a consistency index in excess of K=200,000 induces significant gastrointestinal side effects which would lead to discomfort and lack of patient compliance. The preferred range of consistency indices for administered cellulose ethers is K=60,000 to 130,000. TABLE I illustrates the relationship between viscosity measured at a single shear rate, and the consistency index.

There is a certain level of viscosity required to consistently achieve reductions in postprandial blood glucose levels and/or serum lipid levels. Prior art attempts to effect such reductions have approached the viscosity problem by simply increasing the quantity of fiber ingested to increase viscosity of the administered solution. This approach is unacceptable because an excessively high ingestion of fiber results in intestinal distress. Advantageously, the cellulose ethers which are within the contemplation of this invention develop lumenal viscosities within a discrete range so that a physically-tolerable amount of water-soluble high-viscosity cellulose ether can be used to produce consistent results with minimal side effects.

The compositions of the present invention are intended to be administered to an animal in need of selective reduction of serum lipid levels, specifically total serum cholesterol, LDL cholesterol levels, and triglyceride levels, and/or attenuation of the postprandial rise of blood glucose levels. The compositions of the present invention may reduce both serum lipid levels and serum glucose spiking. However, tests performed at 30 gram dose/day of the cellulose ethers of the present invention, demonstrate that the cellulose ethers do not cause normal human volunteers (non-diabetic) to experience changes in their fasting glucose levels. Thus, the cellulose ethers are safe for administration to non-diabetics for control of hypercholesterolemia. Moreover, it is likely that non-insulin dependent diabetic human patients taking about a 30 gram dose/day of a cellulose ether of the present invention to control post-meal glucose spiking will also experience clinically significant reduction in their LDL and serum cholesterol levels, for example. Since many diabetics have elevated cholesterol levels as a part of their disease state, this reduction in serum lipid levels could be of further benefit.

In the present specification and claims, the term "pretreatment low-density lipoprotein serum cholesterol level" or "pre-treatment LDL serum cholesterol level" is employed to designate the amount or level of low-density lipoprotein (LDL) serum cholesterol exhibited by an animal (or human patient) prior to treatment with the method of the present invention using a water-soluble, high-viscosity grade cellulose ether. Such a pre-treatment LDL serum cholesterol level will generally vary from patient to patient. Such a pre-treatment LDL serum cholesterol level for a human patient may generally be determined by known methods. The LDL serum cholesterol level for normal human patients range from about 75 to about 160 mg/dL, but values above about 130 mg/dL represent increasing risk of coronary heart disease.

The LDL serum cholesterol level is generally determined by $$C_{LDL} = C_{Total} - C_{HDL} - (\text{Triglycerides}/5)$$

wherein:
C=cholesterol in mg/dL;
LDL=low-density lipoprotein serum cholesterol; and
HDL=high-density lipoprotein serum cholesterol.

In the present specification and claims, the term "desired low-density lipoprotein serum cholesterol level" or "desired LDL serum cholesterol level" is employed to designate the amount or level of LDL serum cholesterol exhibited by an animal, particularly a human patient, desired after treatment with the method of the present invention using a water-soluble, high-viscosity grade cellulose ether. Such a desired LDL serum cholesterol level for a given human patient will generally be predetermined by a physician and will depend on the pre-treatment LDL serum cholesterol level. However, such a desired LDL serum cholesterol level will generally be dictated by specific characteristics and health requirements and, as such, will vary from patient to patient. Typically, the desired LDL serum cholesterol level for a human patient will range from about 75 to about 160 mg/dL but will preferably not exceed about 130 mg/dL.

In the present specification and claims, the term "posttreatment low-density lipoprotein serum cholesterol level" or "post-treatment LDL serum cholesterol level" is employed to designate the amount or level of LDL serum cholesterol exhibited by an animal, particularly a human patient, after treatment in accordance with the method of the present invention using a water-soluble, high-viscosity grade cellulose ether.

As used herein, the term "serum lipid levels" refers to total serum cholesterol, serum triglycerides, and LDL and HDL serum cholesterol levels. The term "reduction in serum lipid levels" does not include a reduction in HDL cholesterol level. Particularly, LDL serum cholesterol levels are selectively reduced, and frequently triglycerides are also reduced.

It has been discovered that by using the method of the present invention, the total serum cholesterol level for a human patient may be reduced from about at least 15% up to about 50%, based on the pre-treatment total serum cholesterol level. In fact, in one week of treatment, an average reduction of 25% was observed in the human study reported herein.

It has also been discovered that the method of the present invention provides a "selective" reduction of the concentration of circulating serum LDL cholesterol in the patient's bloodstream. The term "selective" means that the circulating serum LDL cholesterol is reduced (usually in a clinically significant amount of at least about 15% from the pre-treatment level) without producing an alteration in the high-density lipoprotein serum cholesterol levels (HDL). Selective reduction of circulating serum LDL cholesterol up to 50% is achievable through treatment with the cellulose ethers of the present invention. In the same study discussed above, an average reduction in LDL cholesterol levels of 33% was observed after one week of treatment.

It has been discovered that use of the method of the present invention also results in clinically significant reductions of serum triglyceride levels.

In the present specification and claims, the term "postprandial rise in the blood glucose level for an animal" is employed to designate the amount or level of postprandial rise in blood glucose exhibited by the animal after eating. Such a postprandial rise in blood glucose level for an animal will generally vary from animal-to-animal. The postprandial rise in blood glucose level may generally be determined by known methods.

In the present specification and claims, the term "pretreatment postprandial rise in the blood glucose level for an animal" is employed to designate the amount or level of postprandial rise in blood glucose exhibited by an animal prior to treatment with the method of the present invention using a water-soluble, high-viscosity grade cellulose ether.

In the present specification and claims, the term "desired postprandial rise in the blood glucose level for an animal" is employed to designate the amount or level of postprandial rise in blood glucose exhibited by an animal after treatment by the method of the present invention using a water-soluble, high-viscosity grade cellulose ether. Such a desired postprandial rise in blood glucose level for a human patient will generally be predetermined by a physician and will depend on the pre-treatment postprandial rise in blood glucose level. However, such a desired postprandial rise in blood glucose level for the human patient will generally be dictated by specific characteristics and health requirements and, as such, will vary from patient to patient.

In the present specification and claims, the term "post-treatment postprandial rise in the blood glucose level for an animal" is employed to designate the amount or level of postprandial rise in blood glucose exhibited by an animal after treatment with the method of the present invention using a water-soluble, high-viscosity grade cellulose ether.

It has been discovered that by using the method of the present invention, the postprandial rise in the blood glucose level for an animal may be reduced from about 20% up to about 50%, based on the pre-treatment postprandial rise in the blood glucose level.

In the present specification and claims, the terms "amount effective" and "effective amount" represent the minimum amount of the water-soluble, high-viscosity grade cellulose ethers of the present invention, or mixtures thereof, which is necessary to provide the desired serum lipid level and/or the desired postprandial rise in the blood glucose level when administered to an animal. The maximum amount of the cellulose ethers of the present invention to be administered to an animal will be dictated by such considerations as cost, palatability, physical side effects, potential patient non-compliance, and incompatibility of the water-soluble, high-viscosity grade cellulose ethers with other components of the animal's diet.

Due to the above-identified considerations, the cellulose ethers of the present invention, or mixtures thereof, will generally be used in daily consumption in amounts from at least about 5 grams, preferably ranging from about 10 grams to about 50 grams per day for an individual animal.

The compositions of the present invention may be administered to an animal through regular oral administrations of said compositions with meals so as to provide an effective amount of the water-soluble, high-viscosity grade cellulose ether. The high-viscosity grade cellulose ethers may be administered in the present invention in a pre-hydrated form in a composition or as a dry dosage form or composition which will hydrate, following oral ingestion by an animal, in such a manner as to establish the requisite viscosity properties in the upper part of the small intestine of the animal.

A composition comprising the high-viscosity grade cellulose ether may include a food matrix to disguise the taste and consistency of the cellulose ether. A typical food matrix may be gelatin. A preferred composition comprises a dosage amount of a water-soluble, high-viscosity grade cellulose ether, a gelatin, and a drink mix. Both the gelatin and the drink mix may be flavored and/or sweetened with sugar or a sugar-free sweetener. The water-soluble, high-viscosity grade cellulose ether, gelatin, and drink mix may be blended as a dry mixture and then hydrated with an aqueous solution. Preferably, the ratio of aqueous solution to gelatin to water-soluble, high-viscosity grade cellulose ether is, based on weight percent of a total mixture, about 60 to about 99 parts aqueous solution to about 0.5 to about 10 parts gelatin to about 0.5 to about 5 parts high viscosity grade cellulose ether. Of course, other ingredients such as stabilizers and flavors, may be added.

The composition of the present invention may also be in the form of a dough-type formulation, such as a cookie. The term "cookie formulation" includes both the dough-type formulation and the baked or final product for consumption. The water-soluble, high-viscosity grade cellulose ether may be incorporated in the dough at levels from about 2 to about 10 gms per cookie. These cookie formulations typically require a sweetener. By the term "sweetener" is meant sucrose, maltodextrin, high fructose corn syrup or other polysaccharide. Of course, sugar-free recipes can be devised for cookies intended for consumption by diabetics or for other applications requiring such sugar-free recipes. When the cookie formulation has a low fat content, which is desirable for an animal trying to reduce its serum cholesterol levels, the sweetener may also serve as a binder. Such a solid dosage form would need to be ingested along with an appropriate amount of a liquid to assure adequate moisture availability for hydration of the high-viscosity grade cellulose ether in the upper digestive tract of the animal.

It is generally recognized that those skilled in the medical and pharmaceutical arts do not currently understand the full mode of action of soluble dietary fibers in the process of lowering serum lipid levels or attenuating the postprandial rise in serum glucose levels. What is evident from the studies underlying this invention is that by providing to the animal a generous supply of inert, water-soluble, high-viscosity grade cellulose ether, natural intralumenal processes are mobilized and assisted to achieve reductions in circulating total and LDL cholesterol levels and attenuation of postprandial rise in serum glucose levels via a non-systemic, non-invasive therapy, with concomitant likelihood of minimal unwanted systemic side effects.

While not wishing to be bound by any particular theory, it is believed that the mode by which the water-soluble, high-viscosity cellulose ethers of the present invention affects both blood cholesterol lowering and attenuation of postprandial rise of blood glucose levels in animals appears to depend on achieving a high intralumenal (gut) viscosity at the site and time of digestion of the ingested meal. Thus, in preferred embodiments, the cellulose ether of the present invention is administered along with the meal, and more preferably in divided portions during the course of the meal. The term "meal" means a main ingestion of food where a significant portion of the animal's daily caloric input is ingested.

To achieve the required high intralumenal viscosity, the cellulose ether of the present invention must be substantially uniformly hydrated. Thus, the cellulose ether of the present invention must not be present as "fish-eyes" or "globules" of partly hydrated cellulose ether, suspended or otherwise distributed, in large volumes of low viscosity chyme. Both glucose absorption from the gut into the bloodstream of an animal and processing of fats, including cholesterol, for transport out of the gut into the bloodstream occur mostly in the upper part of the small intestine. Thus, by the time an ingested meal with the cellulose ether of the present invention leaves the stomach and enters the small intestine, the cellulose ether should be in the desired condition, namely, thoroughly hydrated, dissolved and dispersed uniformly into the chyme.

One method to assure that this desired condition of the cellulose ether is achieved is to have the cellulose ether ingested in a prehydrated form, for example as in a gelatin matrix. Thus, the compositions of the present invention frequently use the cellulose ether of this invention in their prehydrated form when administered to an animal. When the cellulose ether of the present invention is in a powder form, it is dispersed in an edible solid dosage form, such as a cookie or muffin. This solid dosage form is then ingested by the animal at meal time along with sufficient liquid to permit thorough hydration of the cellulose ether of the present invention to occur in the stomach. Typically, the solid dosage form will contain 2 grams to 10 grams of the cellulose ether of the present invention and about 200 to about 500 ml of liquid is to be consumed.

Another method to assure that the desired condition of the cellulose ether is achieved at the right time is to have a powdered, reverse-enteric coated or micro-encapsulated cellulose ether of the present invention suspended in a milkshake or fruit-flavored drink formulation such that upon ingestion of about a 500 ml drink having about 10 grams of the suspended cellulose ether therein, decoating of the cellulose ether occurs at the pH of the animal stomach, i.e., pH of 2–5, followed by rapid hydration of the cellulose ether in the stomach. Such coating techniques are well-known to persons of skill in the art. U.S. Pat. No. 4,732,917, for example, discloses a technique for preparing sucrose encrusted MC particles to improve dispersibility.

Thus, any dosage form which achieves the desired condition of the water-soluble, high-viscosity cellulose ether of the present invention is an acceptable composition for administering the cellulose ether to an animal. Obviously, the dosage form should be convenient and palatable to the animal and provide from about 2 to about 20 grams of the cellulose ether per dose. Some possible dosage forms are: powdered drink mixes, cookies, granola bars, fruity snacks, gelatins, puddings, breads, biscuits, popsicles, ice creams, frozen yogurts, muffins, jellies, jams, or crackers; and if micro-encapsulated or reverse enteric-coated, as powdered food additives, bottled drinks, tablets, capsules or caplets.

This invention will be further clarified by a consideration of the following examples, which are intended to be purely exemplary of the present invention.

EXAMPLE 1

Gelatin Formulation

A 10.0 gram total blend of 85 weight percent of a high-viscosity grade hydroxypropylmethylcellulose ether, having a methoxyl substitution of about 19 to about 24 weight percent and a hydroxypropoxyl substitution of about 4 to about 12 weight percent and a viscosity of about 100,000 cP (100,000 mPa·s) as a 2 weight percent aqueous solution at 20° C., (METHOCEL™ K-100M, available from The Dow Chemical Company) and 15 weight percent of a second high-viscosity grade hydroxypropylmethylcellulose ether, having a methoxyl substitution of about 19 to about 24 weight percent and a hydroxypropoxyl substitution of about 4 to about 12 weight percent and a viscosity of about 15,000 cP (15,000 mPa·s) as a 2 weight percent aqueous solution at 20° C., (METHOCEL™ K-15M, available from The Dow Chemical Company) is added to a dish containing 8.5 grams of a sugar-free strawberry flavored gelatin, and 1.0 gram of a sugar-free punch-flavored drink mix. The powders are thoroughly blended. To this blend is added boiling water (375 grams) and the mixture is stirred until smooth. Ice (125 grams) is then added and stirred until smooth and the resulting product is cooled until firm.

The product is a firm gelatinous material. The mouthfeel of the hydroxypropylmethylcellulose ether is effectively masked.

EXAMPLE 2

Cookie Formulation 85 grams of a powdered, high-viscosity grade hydroxypropylmethylcellulose ether, having a methoxyl substitution of about 19 to about 24 weight percent and a hydroxypropoxyl substitution of about 4 to about 12 weight percent and a viscosity of about 100,000 cP (100,000 mPa·s) as a 2 weight percent aqueous solution at 20° C. (METHOCEL™ K-100M Premium Grade, available from The Dow Chemical Company) are dry blended with 150 grams of ground whole wheat flour and ½ teaspoon of nutmeg to form a blended powder mixture. 50 grams of walnuts are coarsely diced and combined with 100 grams of dried raisins that have been presoaked. 150 grams of honey are combined with 110 grams of water and brought to a boil, with stirring. The hot honey aqueous solution is poured onto the blended powder mixture and mixed with a spoon, resulting in a moist dough. The walnut and raisin mixture is thoroughly blended into a moist, lumpy dough.

The dough is then formed into 10 "balls" which are pressed onto a cookie sheet. The dough is baked in a pre-heated oven at 350° C. for 15 minutes. The resulting cookies have the usual appearance and characteristics of chewy cookies. Each cookie contains about 8.5 g hydroxypropylmethylcellulose.

In a method of use aspect, one cookie is to be consumed by the patient with a patient's normal meal. In a particularly preferred method of use, the solid dosage form containing the cellulose ether is ingested in divided portions during the course of the meal, rather than as a "bolus" dose prior to, or following, the meal. This ensures thorough and adequate mixing of the cellulose ether with the stomach contents. Effectiveness is maximized, particularly with respect to LDL, cholesterol, and triglyceride level reductions, and glucose level control, when the cellulose ether is uniformly distributed in the chyme as it enters the small intestine from the stomach. The upper small intestine is where bile salt-mediated hydrolysis and transport of fats into the portal system occurs. Moreover, the bile salts reabsorb into the bloodstream from the small intestine.

Of course, the solid dosage form could be in the form of a cheese flavored cracker, or a biscuit, for instance, rather than the form of a cookie to ensure that the patient consumes the dosage form over an appropriate time frame in conjunction with the meal.

A. Use of High-Viscosity Cellulose Ethers to Attenuate the Postprandial Rise of Blood Glucose Levels The relationship between the postprandial rise of blood glucose levels and meal viscosity was studied by adding various combinations of hydroxypropylmethylcellulose (HPMC) to simple glucose meals and administering them to female mongrel dogs. The test meals were administered through an orogastric tube after fasting the dog for 16 hr from food, but not water. Blood samples were withdrawn via an indwelling catheter in the dog's foreleg prior to administration of the meal and at various time intervals thereafter. The samples were analyzed by known means for serum glucose levels.

The effect of HPMC was examined at four viscosity levels: non-viscous (no HPMC), low (5,000 cP or mPa·s), medium (15,000 cP or mPa·s), and high (30,000 cP or mPa·s); viscosity being measured at 37° C. and 1 sec$^{-1}$. TABLE I gives the mean viscosities of the various HPMC meals used in the study in cP at 37° C. for shear rates of 1 sec$^{-1}$ and 100 sec$^{-1}$. The standard deviation is shown in parentheses. Consistency indices, over a shear rate range of 100 sec$^{-1}$ to 1000 sec$^{-1}$ at 37° C., reflect the pseudoplastic properties of HPMC. The higher the consistency index value, K, the more viscous the solution.

TABLE I

| Meal | cP (mPa · s) at 1 sec$^{-1}$ | cP (mPa · s) at 100 sec$^{-1}$ | Consistency Index, K |
|---|---|---|---|
| Low | 6,827 | 1,081 | 16,981 |
|  | (3486) | (75) | (1,960) |
| Medium | 15,122 | 1,773 | 44,871 |
|  | (4798) | (105) | (3,286) |
| K4 Meal | 16,881 | 3,292 | 110,975 |
|  | (6399) | (246) | (33,489) |
| High | 29,276 | 2,337 | 78,337 |
|  | (5282) | (181) | (9,450) |

A viscosity-response profile over a wide range of viscosities was obtained by using combinations of HPMCs of various molecular weights as opposed to altering the concentration of cellulose ether, or changing the type of cellulose ether. Levels of glucose administered were no glucose, a 1:20 aqueous solution and a 1:5 aqueous solution. Test meals comprised HPMC in the glucose solutions. In addition to the test meals, meals containing no HPMC were administered to determine the normal postprandial glucose response of each dog (positive controls). Further, HPMC meals were administered with no glucose, but with saline to match the osmolarity of the glucose solutions, to determine whether the HPMCs had any direct effect on fasting glucose levels (negative controls).

Specifically, the meals comprised:

a. Positive Control Meals

1:20 Meal: 50 g glucose (D (+)-Glucose, Sigma Chemical Company, St. Louis, Mo.), 8 g PEG 4,500 (Polyglycol E 4500, The Dow Chemical Company, Midland Mich.), and 1 L distilled water.

1:5 Meal: 200 g glucose, 8 g PEG 4,500 and 1 L distilled water.

b. Test Meals

HPMC was dissolved in either the 1:20 glucose or 1:5 glucose solutions described above. Illustratively, the desired quantity of HPMC was dispersed in one-third of the glucose solution and heated to 80° C., then the remainder of the glucose solution was mixed in and the solution was allowed to cool.

The viscous solutions were prepared at a total of approximately 2% concentration using blends of K4M, K15M and K100M premium grade HPMC (METHOCEL™, The Dow Chemical Company, Midland Mich.). The grades of HPMC are identical with respect to chemical composition of the repeating unit and differ only in terms of the average molecular weight of the product.

The Low Meal:

A meal having a viscosity of approximately 5000 cP (5000 mPa·s) at 37° C. and a shear rate of 1 sec$^{-1}$ comprised 0.78% K4M and 1.14% K15M.

The Medium Meal:

A meal having a viscosity of approximately 15,000 cP (15,000 mPa·s) at 37° C. and a shear rate of 1 sec$^{-1}$ comprised 1.35% K15M and 0.65% K100M.

The K4 Meal:

A second medium viscosity HPMC dispersion was prepared with 3.3% K4M.

The High Meal:

A meal having a viscosity of approximately 30,000 cP (30,000 mPa·s) at 37° C. and a shear rate of 1 sec$^{-1}$ comprised 0.30% K15M and 1.70% K100M.

c. Negative Control Meals

Negative control meals were prepared by incorporating appropriate amounts of NaCl (9 or 35 g) to match the osmolalities of the glucose solutions. The 0.9% NaCl solution was administered as a nonviscous and as a high viscosity HPMC solution. The 3.5% solution was administered only as a high viscosity HPMC solution, in order to avoid emesis.

Figure 2:
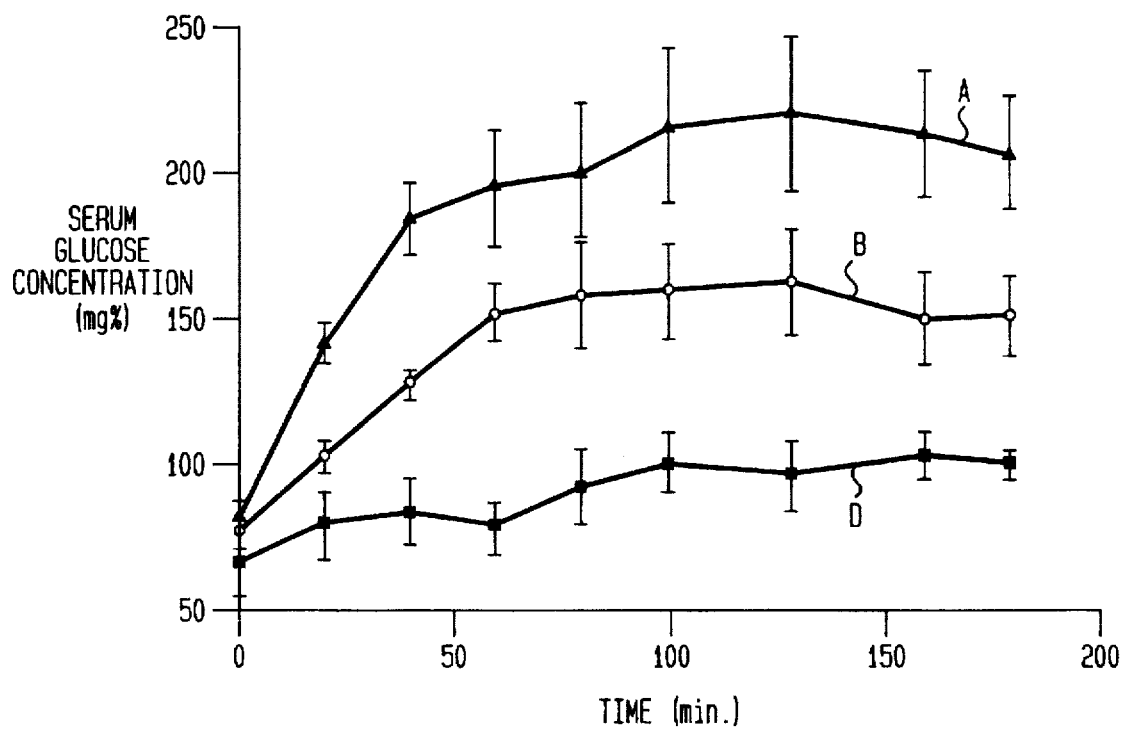
FIG. 2 is a graphical representation of serum glucose concentration level vs. time curves in dogs following, in one curve ("B"), coadministration of the same high-viscosity cellulose ether as in FIG. 1 in 1:5 aqueous glucose solutions.

The results are shown in FIGS. 1 and 2 which are graphical representations of postprandial serum glucose concentration expressed as mean serum glucose levels (concentration in mg%) vs. time (min.) curves for The High Meal in the 1:20 glucose solution and in the 1:5 glucose solution, respectively. Referring to FIGS. 1 and 2, the line designated "A" represents the results following administration of the glucose positive control solution; line "B" is for The High Meal; line "C" is for the negative control, normal saline (0.9%); and line "D" is for the negative control, 3.5% NaCl plus high viscosity HPMC.

Referring to FIGS. 1 and 2, high-viscosity HPMC significantly reduced the peak serum glucose level, $C_p$, by 60% for the 1:20 meal and by 40% for the 1:5 meal, and at the same time reduced the area under the serum level vs. time curve (AUC$_{0-3}$ hr) by 40 to 50%. AUC is an indication of the extent of glucose absorption. $T_p$ is the time at which $C_p$ occurs.

Medium viscosity HPMC (The Medium Meal and The K4 Meal) reduced $C_p$ at both glucose concentrations, but reduced AUC only for the 1:20 meal. Low viscosity HPMC (The Low Meal) lowered $C_p$ only after the 1:20 meal and had no significant effect on AUC at either glucose level.

The mean pharmacokinetic parameters for all three meals are given below in TABLES II and III. The data is expressed as percent of the corresponding positive control values after adjusting for the negative control values. The data was expressed in this manner due to large variations in glucose levels from dog-to-dog. For example, if the mean fasting glucose level for a given dog was 65 mg % and the positive control peak level was 165 mg % for the same dog, the adjusted value after the test meal would be calculated as a percentage of the positive control using the formula:

$$C_{p(test)adj} = [(C_{p(test)} - 65)/(165-65)] \times 100$$

TABLE II

MEAN PHARMACOKINETIC PARAMETERS FOR 1:20 GLUCOSE MEALS[1]

| Meal | $C_p$ | $T_p$ | AUC$_{0-3}$ Hr. | n[2] |
|---|---|---|---|---|
| Low | 55 (35)* | 262 (161) | 92 (42) | 4/5 |
| Medium | 56 (19)* | 233 (153) | 63 (39) | 3/4 |
| K4 Meal | 56 (34) | 236 (164) | 82 (46) | 3/4 |
| High | 38 (12)* | 340 (174)* | 46 (20)* | 5/6 |

[1]Standard Deviation is given in parentheses. Asterisks denote statistically significant differences from the positive control meals.
[2]Number of dogs/Number of experiments.

TABLE III

MEAN PHARMACOKINETIC PARAMETERS FOR 1:5 GLUCOSE MEALS[1]

| Meal | $C_p$ | $T_p$ | $AUC_{0-3}$ Hr. | n[2] |
|---|---|---|---|---|
| Low | 84 (41) | 102 (20) | 74 (36) | 4/6 |
| Medium | 52 (11)* | 58 (18) | 47 (12)* | 3/4 |
| K4 Meal | 61 (23)* | 78 (46) | 57 (20) | 3/4 |
| High | 63 (14)* | 92 (25) | 57 (16)* | 5/10 |

[1]Standard Deviation is given in parentheses. Asterisks denote statistically significant differences from the positive values.
[2]Number of dogs/Number of experiments.

The $AUC_{0-3\ hr}$ values were reduced by addition of HPMCs to the 1:20 glucose meals. The reduction was dramatic in the case of the high viscosity meal, while for the medium and low viscosity meals produced no significant difference from the positive control values. Linear regression between meal viscosity and $AUC_{0-3\ hr}$ indicated that a significant inverse correlation exists between these two parameters. This relationship is shown in FIG. 3 which is a graphical representation of AUC as a percent of the corresponding positive control value plotted against input viscosity of the meal measured at 37° C. and at 1 $sec^{-1}$.

Figure 4:
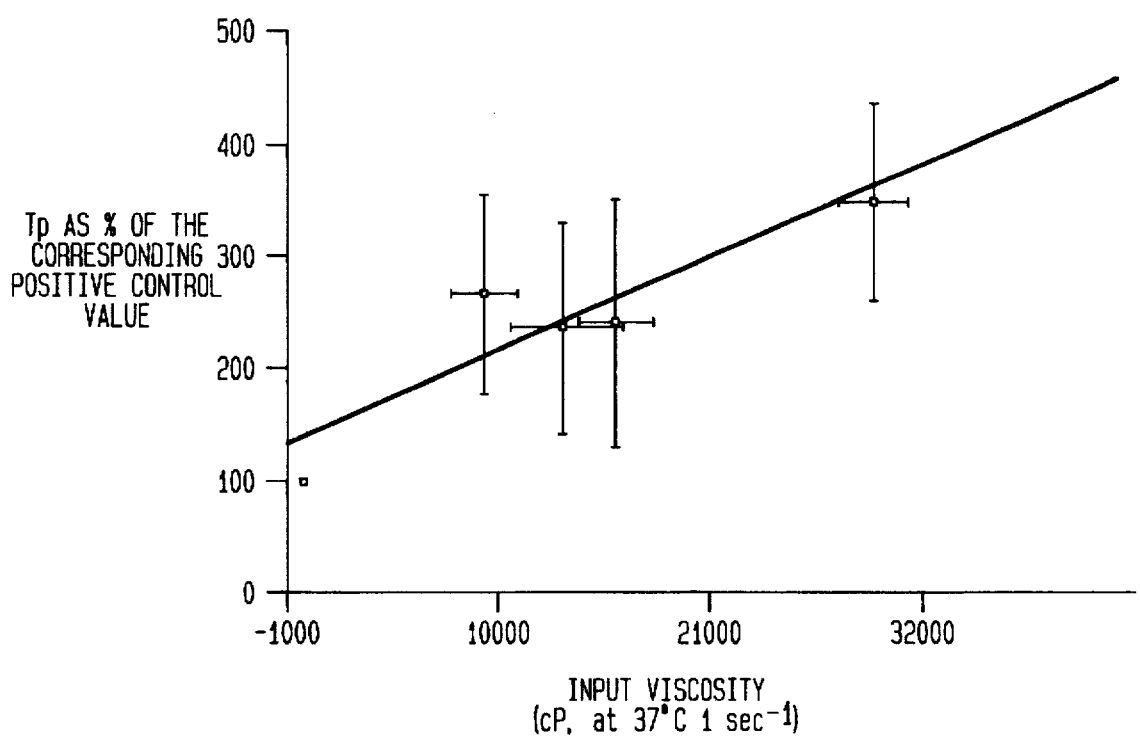
FIG. 4 is a graphical representation of the relationship between $T_p$, the time at which the peak serum glucose level, $C_p$, occurs in dogs for a 1:20 glucose solution containing a cellulose ether and input viscosity, measured at 37° C. and at 1 sec.

FIG. 4 shows the relation between $T_p$ and meal viscosity, measured at 37° C. and at 1 $sec^{-1}$, for the 1:20 glucose solutions. $T_p$ is expressed as a percent of the corresponding positive control value. Addition of HPMC to the 1:20 glucose meals resulted in an average delay in $T_p$ by a factor of two to three. Addition of HPMC to the 1:5 glucose solution did not result in a further increase in $T_p$. Presumably, negative feedback effects on gastric emptying are already maximal when a 1:5 glucose solution is administered.

Figure 3:
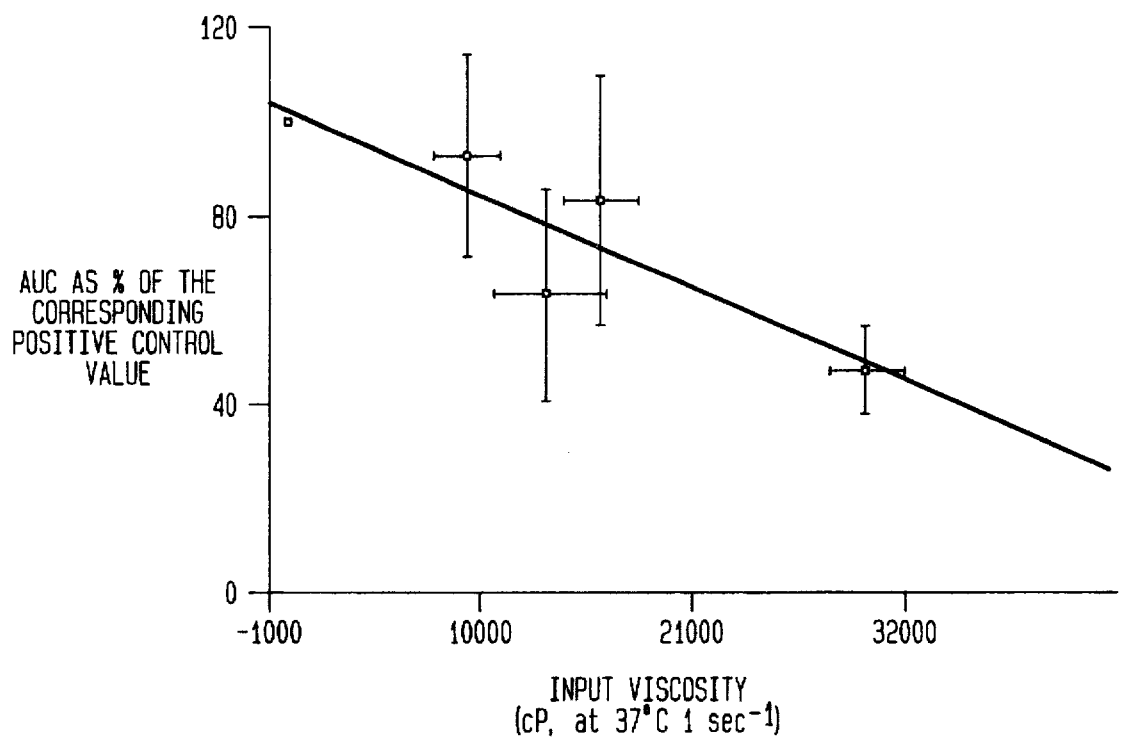
FIG. 3 is a graphical representation of, on the vertical axis, the area under the serum glucose concentration level vs. time profile (AUC) as a percent of the corresponding positive control value, plotted against, on the horizontal axis, input viscosity of a 1:20 glucose solution containing a cellulose ether, measured at 37° C. and at 1 sec$^{-1}$.

The relationships shown in FIGS. 3 and 4 indicate that input viscosity of the meal is key to the ability of the water soluble cellulose ether to control the serum glucose profile. In the case of the 1:5 glucose meals, the medium and high viscosity meals were about equally effective in controlling the serum glucose profile, while the low viscosity HPMC solution had no significant effect. The reduction in $C_p$ and $AUC_{0-3\ hr}$ was less dramatic for the high viscosity meal when it was added to the 1:5 meal than when it was added to the 1:20 meal. Thus, the concentration of glucose in the meal may have some impact on the maximum effect achievable by the water soluble cellulose ether. It should be noted, however, that the concentration of glucose used in this study (i.e., 1:5 or 20%) exceeds both percentage and amount of glucose in a standard glucose tolerance test. Thus, minor dietary restrictions would enhance the efficacy of a treatment program using the dietary supplements of the present invention.

The results for the two medium viscosity meals (The Medium Meal and The K4 Meal) were compared to determine the relative importance of HPMC molecular weight and concentration effects. The addition of the 2% high molecular weight HPMC to the glucose meals resulted in more effective control of serum glucose than the addition of the 3.3% low molecular weight (K4M) HPMC. Thus, a more efficient means of controlling the postprandial serum glucose profile is to use a higher molecular weight, higher-viscosity grade, water-soluble cellulose ether, rather than to increase the dosage of a lower molecular weight cellulose ether.

For example, a 2% aqueous solution of a high molecular weight HPMC advantageous in the practice of the invention has a viscosity of about 30,000 cP (30,000 mPa·s) at 37° C. and 1 $sec^{-1}$. Rheological studies have confirmed that a very high molecular weight HPMC (about 400,000 cP (400,000 mPa·s) at 20° C. and 1 $sec^{-1}$ in a 2% aqueous solution) produces a viscosity equivalent to 30,000 cP at a concentration of 1.5%.

In fact, further studies of chyme samples from fistulated dogs have demonstrated that administration of the very high molecular weight HPMC at a relative dose concentration of 1.5% in either pre-hydrated form or as a chewable comestible, i.e., a cookie, produces the same in vivo viscosity at mid-gut as the high molecular weight HPMC at 2.0% (15,000 cP (15,000 mPa·s) at 37° C. and 1 $sec^{-1}$).

Overall, the results indicate that the ability of water-soluble, high-viscosity cellulose ethers, such as hydroxypropylmethylcellulose, to attenuate the postprandial rise in blood glucose levels is dependent on the intralumenal viscosity of the solution. The medium and high viscosity HPMC combinations appear to be more effective than the low viscosity HPMC, especially when a 1:5 glucose meal was administered. This shows that only HPMCs which can generate a certain level of viscosity in the lumen will be useful in the treatment of diabetes. However, at higher intralumenal viscosity levels (at 60,000 cP (60,000 mPa·s) or higher, as measured at 37° C. and 1 $sec^{-1}$) the dogs experienced gastrointestinal distress (whining, turning to the flank), indicating that there is also an upper limit to the therapeutically useful range of intralumenal viscosities.

The ability of a water-soluble, high-viscosity cellulose ether to control the postprandial rise in blood glucose levels in human NIDDM patients following a standard meal was studied in a double blind cross-over study. The test formulation comprised 10 g of a hydroxypropylmethylcellulose mixture exhibiting a 2 weight percent aqueous viscosity of 80,000 cP (80,000 mPa·s) at 20° C. (a mixture of METHOCEL™ K100M and METHOCEL™ K15M cellulose ethers, each available from The Dow Chemical Company, Midland, Mich.; herein designated "HPMC K8515") in 500 ml of a diet (sugar-free) gelatin formulation in accordance with Example 1. The test formulation was administered to ten subjects in conjunction with a high carbohydrate meal. Blood samples were drawn at 15, 20, 45, 60, 75, 90, 120, 150, 180, 210, 240, and 360 minutes post-administration.

Table IV below shows the mean pharmacokinetic parameter data for glucose and insulin profiles analyzed for differences using a Student's t-test for paired data. The data show a decrease in peak level and area under the curve following administration of the test formulation to human NIDDM subjects.

TABLE IV

| | GLUCOSE | | INSULIN | |
|---|---|---|---|---|
| Parameter | Mean (SD) | p | Mean (SD) | p |
| % $C_p$ | 75.9 (18.3) | 0.0042 | 106.0 (38.4) | 0.65 |
| % $T_p$ | 136.8 (82.3) | 0.217 | 106.90 (75.4) | 0.789 |
| % AUC | 89.9 (14.7) | 0.0729 | 118.9 (53.6) | 0.3212 |

*Note:
SD = standard deviation
p = statistical significance

B. Hydrodynamic Responses to Water-Soluble High Viscosity Cellulose Ether Meals

The hydrodynamic responses in the gastrointestinal tract to administration of the water-soluble cellulose ether-containing meals are dependent on the viscosity of the meal administered. The effects of the exemplary cellulose ether, HPMC, on (1) intralumenal viscosity, (2) gastric emptying rate, (3) intestinal transit, and (4) net water flux in six dogs fistulated at proximal duodenum and/or mid-jejunum are reported herein.

Four different 500 ml meals were administered to the dogs via an orogastric tube at three viscosity grades of HPMC, and having a total HPMC concentration of either 2% or 3.3% by weight. Reference should be made to the Test Meal compositions given hereinabove (Section A.) for HPMC composition. Note, however, that glucose was omitted from the formulas in this study. Control meals consisted of 500 ml solutions of 0.9% NaCl and 0.8% PEG (Polyglycol E 4500, The Dow Chemical Company, Midland, Mich.). NaCl was used to adjust the solutions to iso-osmolality (approx. 270 mOsm/kg) and PEG was used as a volume marker.

Chyme was collected at various times following administration of the meal. The chyme was measured for volume and was analyzed for viscosity and PEG content.

Values for shear rate in the range 50 to a few hundred $sec^{-1}$ have been suggested by the art for the mouth during mastication, however, the shear rate in the upper GI tract has not been measured satisfactorily. Furthermore, shear rate is thought to vary considerably with physiological conditions in the upper GI tract, so quotation of the viscosity characteristics at a single shear rate may be inappropriate.

Measurement of intralumenal viscosity is given herein in terms of the consistency index, K, which is a constant derived from the overall viscosity/shear profile (range 100 $sec^{-1}$ to 1000 $sec^{-1}$). Consistency indices are proportional to the viscosity and are calculated from the power law using $$T = KD^n \qquad (1)$$

where T is the shear stress; D is the shear rate; and K (the consistency index) and n are constants characteristic of the material, with n always less than one for pseudoplastic materials. Substituting the definition of viscosity, v, i.e., v=T/D, the above equation becomes $$vD = KD^n \qquad (2)$$

Then by taking the natural logarithm of both sides, one obtains $$\ln D = \ln v/(n-1) - \ln K/(n-1) \qquad (3)$$

from which the consistency index (K value) can be calculated. The mean input viscosities of the meals administered, measured at both low (1 $sec^{-1}$) shear rates and high shear rates (100 $sec^{-1}$), and calculated as the consistency index are shown in Table I above.

The consistency index of chyme recovered after the control meal was very low, approximately 40, at both duodenum and midgut. Meals containing HPMC always produced more viscous chyme than control meals. The HPMC elevated the viscosity of the lumenal contents over the complete course of meal transit. However, the viscosity of the recovered chyme was always lower than the input viscosity of the administered meal.

Figure 5:
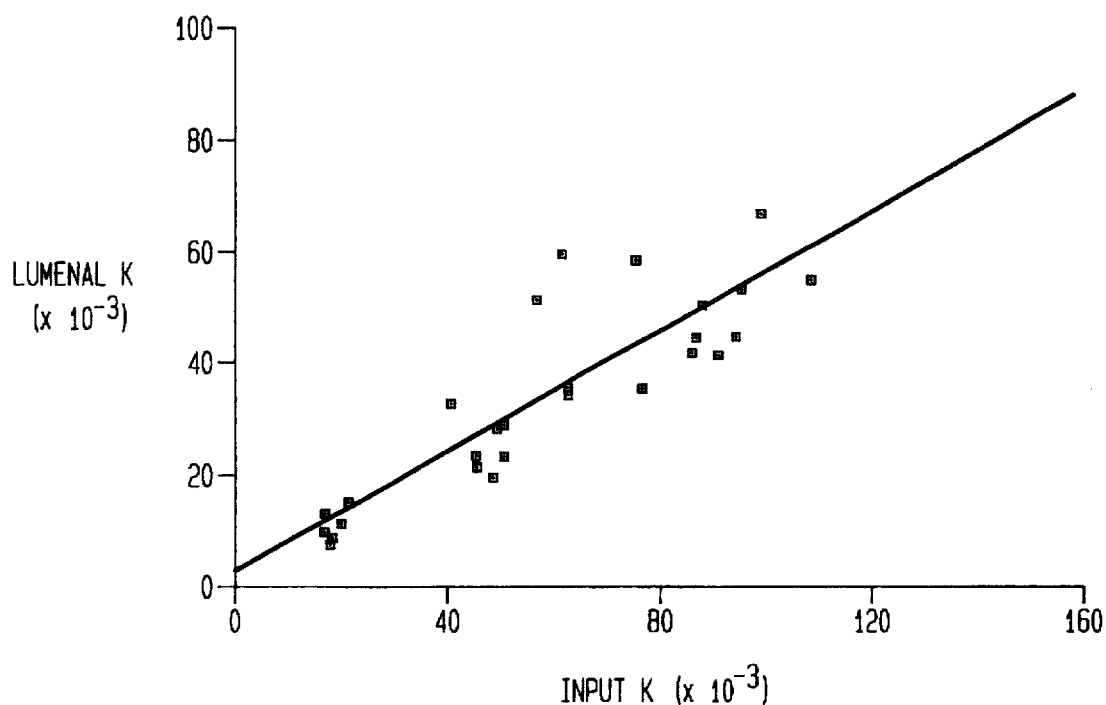
FIG. 5 is a graphical representation of lumenal content (chyme) viscosity, expressed as consistency index (K) values, for chyme recovered at the upper duodenum of fistulated dogs versus input meal viscosity.
Figure 6:
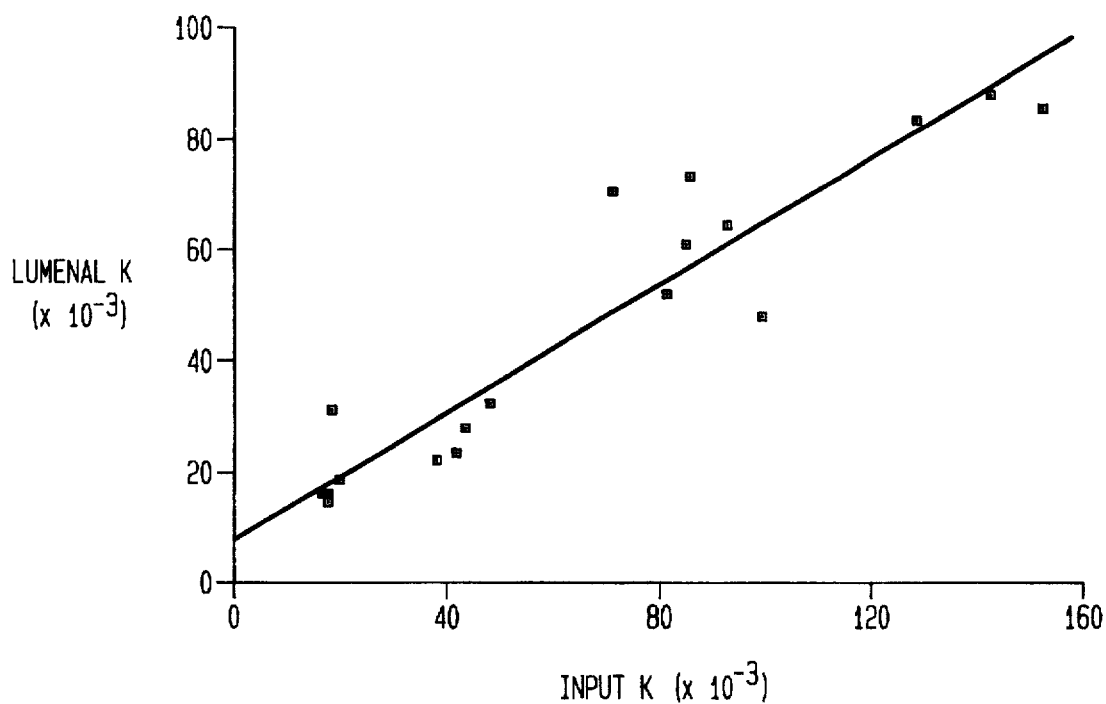
FIG. 6 is a graphical representation of lumenal content viscosity, expressed as consistency index (K) values, for chyme recovered at the mid-jejunum of fistulated dogs versus input meal viscosity.

Referring to FIGS. 5 and 6, the correlation between input and lumenal viscosities is shown. As the consistency index of the input meal increases, there is a proportional increase in lumenal consistency index, both at the duodenum (FIG. 5) and midgut (FIG. 6). The slope of the line with the best fit indicates that the viscosity of the meal decreased by approximately a factor of 2 between ingestion and recovery (for the duodenum, n=29 experiments on 4 dogs, slope=0.52, r=0.880, and p<0.0004; for mid-jejunum, n=19 experiments on 4 dogs, slope=0.54, r=0.937, and p<0.0004).

Measurement of PEG concentration in the chyme indicated that the presence of HPMC in the meals has negligible effect on water flux in the stomach or the upper duodenum and, at most, a slight tendency to impede water absorption from the jejunum.

Figure 7:
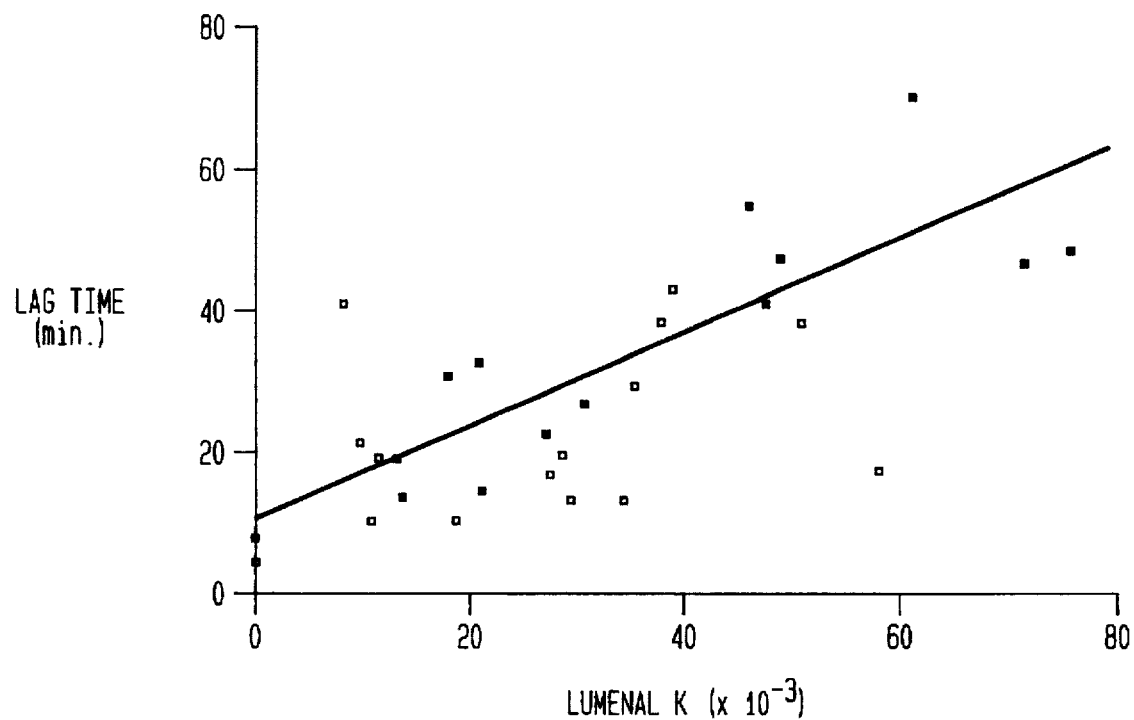
FIG. 7 is a graphical representation of mean lag time responses for chyme recovery, in minutes, observed at the duodenum (□) and mid-jejunum (■) of fistulated dogs plotted against lumenal content viscosity expressed as a consistency index.

The time lag for complete chyme recovery increased linearly with lumenal viscosity as shown in FIG. 7. FIG. 7 shows the correlation between lumenal viscosity expressed as a consistency index value and the lag time in minutes observed at the duodenum (□) and mid-jejunum (■). Each point represents the mean time lag response of one dog to one meal type. Four dogs were used in the study (line of best fit: y=9.98+0.00055x, r=0.701, and p<0.001). The relationship between the lumenal viscosity and lag time was superimposable for the two recovery sites which suggests that most of the delay in fluid transit due to viscosity effects occurs in the stomach.

Figure 8:
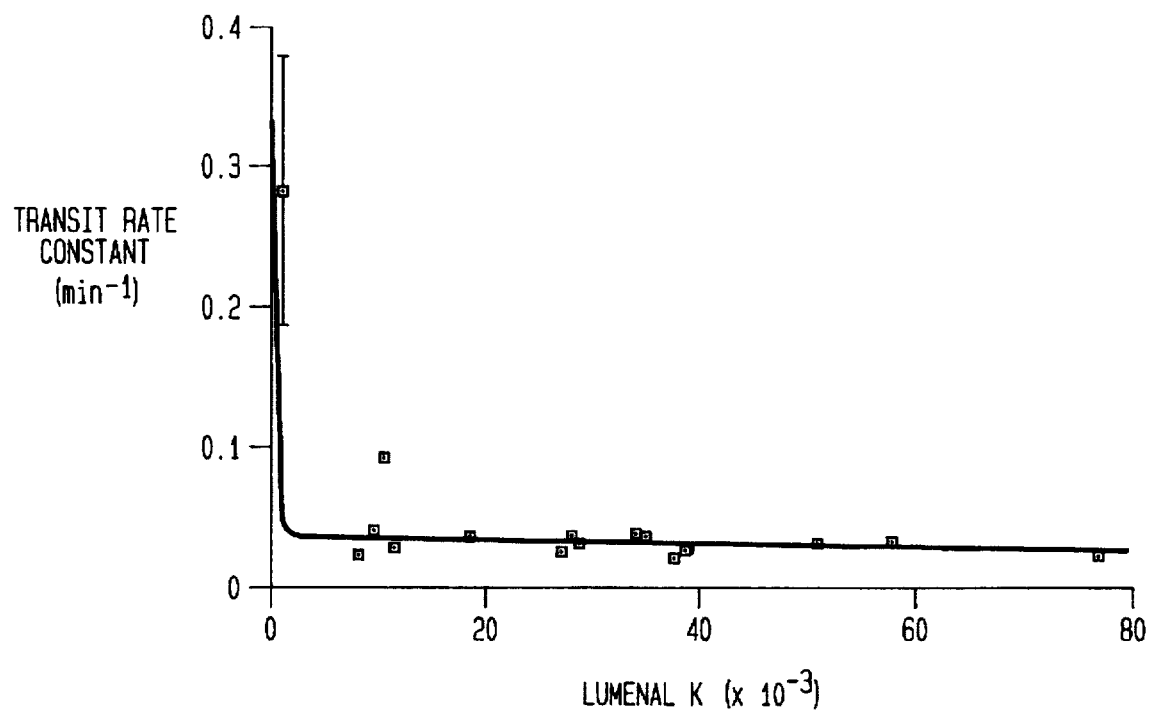
FIG. 8 is a graphical representation of transit rate constants, in min$^{-1}$, for chyme recovery from the upper duodenum of fistulated dogs plotted against lumenal content viscosity, expressed as a consistency index value.
Figure 9:
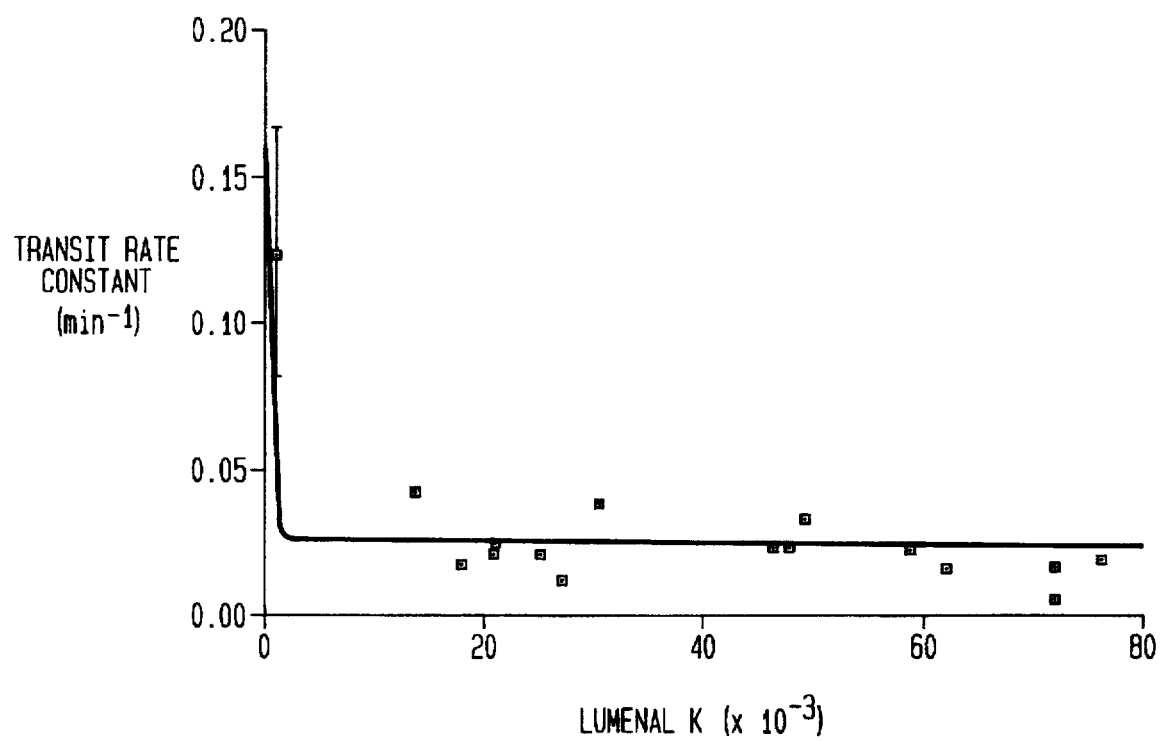
FIG. 9 is a graphical representation of transit rate constants, in min$^{-1}$, for chyme recovery from the mid-jejunum of fistulated dogs plotted against lumenal viscosity, expressed as a consistency index value.

A pronounced decrease in the first order transit rate constants ($min^{-1}$) was observed as the lumenal viscosity increased from that of water to that caused by the low viscosity meals. However, there was little further change as the meal viscosity increased further. Statistical analysis indicated that there was a significant difference in the transit rate constants between the two fistula sites. FIG. 8 shows the correlation between lumenal viscosity expressed as a consistency index value (K) and the transit rate constants for the upper duodenum (line of best fit: $k_{tr}$=0.027+8.9(1/n), r=0.920). FIG. 9 shows the correlation for the mid-jejunum (line of best fit: $k_{tr}$=0.022+4.2(1/n), r=0.818). Each point represents the mean time lag response of one dog to one meal type. Four dogs were used in the study.

The results of this study demonstrate that administration of a water soluble cellulose ether in accordance with this invention will produce an effect on both the lumenal viscosity and the rate of transit through the upper gastrointestinal tract, without significantly influencing water flux across the gut wall. The exemplary HPMC cellulose ether administered to dogs increased the lumenal viscosity, over much of the upper gastrointestinal tract, by two to three orders of magnitude as compared to the viscosity of the control meals.

Although the input viscosity of the HPMC meals was reduced by approximately 50% during passage through the upper gastrointestinal tract, lumenal viscosities were still several orders of magnitude higher than the control value. The majority of the decrease in flow rate occurs when the viscosity of the meal is elevated from the control (K=40) to low viscosity (K=20,000). When the lumenal consistency index is increased to about 100,000, such as with administration of The K4 Meal or The High Meal, only modest further decreases in the emptying rate constants were observed.

In summary, the increase in lumenal viscosity following administration of HPMC meals was two to three orders of magnitude. In contrast, the transit parameters decreased by a factor of five or six. These results suggest that diffusivity effects are more important than transit effects in modifying absorption profiles of nutrients.

C. Use of Water-Soluble, High Viscosity Cellulose Ethers to Reduce the Low-density Lipoprotein and Serum Cholesterol Levels in Humans Three short-duration studies were conducted to assess the efficacy of a high molecular weight cellulose ether as a cholesterol-lowering agent, the dose response curve of its action, and the ability of adults to tolerate its ingestion at effective doses. Both normal and mildly hyperlipidemic subjects were studied. Administration of 10 g of a high molecular weight cellulose ether composition (HPMC K8515) in a prehydrated form with meals, three times a day, lowered cholesterol levels by an average of 56 mg/dL in normal subjects within one week. In two studies with mildly hyperlipidemic subjects, average reductions of 39 mg/dL and 45 mg/dL were observed within the same time period. The effect was primarily due to a reduction in LDL cholesterol levels. Although there was an observed tendency for HDL cholesterol levels to decrease slightly, this decrease was only significant in subjects with normal serum cholesterol levels who would not typically be subject to this therapy. Changes in cholesterol levels were not accompanied by a rise in triglyceride levels. Dose-response studies indicated that it is possible to achieve a 15% decrease in LDL cholesterol levels within one week at a dose of 20 g/day HPMC K8515 with minimal adverse side-effects.

C(i). Effects of Water-Soluble, High Viscosity Cellulose Ethers to Reduce the Low-density Lipoprotein and Serum Cholesterol Levels In Healthy Subjects The effects of intake of the water-soluble, high viscosity cellulose ether compositions of the present invention on the serum lipid profile was investigated in a one-week crossover study of ten healthy men between the ages of 21 and 31. Health status upon entering the study was confirmed by physical examination and a biochemical blood screen. Two subjects were borderline hypercholesterolemic upon entry to the study.

The study was conducted on a double blind basis, with the two phases administered in a block crossover design. In one phase of the study, subjects received the test formulation with each of three meals per day. The test formulation comprised 10 g of a hydroxypropylmethylcellulose mixture exhibiting a 2 weight percent aqueous viscosity of 80,000 cP (80,000 mPa·s) at 20° C. (HPMC K8515) in 500 ml of a diet gelatin formulation in accordance with Example 1. In the other phase, subjects received a placebo diet gelatin formulation. Food consumption was matched exactly between the two phases, and there were no restrictions as to what could be ordered from the Clinical Research Center's menu.

Serum levels of total, LDL, and HDL cholesterol and triglycerides were measured at the time of the initial physical, and in the fasting state before and after each phase of the study. The results are presented in TABLES IV(A)–IV(D) below. For reference, normal serum level ranges are:

| | | |
|---|---|---|
| Total Cholesterol | 0–240 mg/dL | (desirable: <200) |
| LDL | 75–160 mg/dL | (desirable: <130) |
| HDL | 35–72 mg/dL | |
| Triglycerides | 30–150 mg/dL | |
| Glucose | 73–115 mg % | |

TABLE IV(A)

TOTAL CHOLESTEROL LEVELS BEFORE AND AFTER EACH PHASE

| | | Total Serum Cholesterol | | | | First |
|---|---|---|---|---|---|---|
| | Prestudy | Placebo(P) | | Test(T) | | Treatment |
| Subject | Average(Range) | Before | After | Before | After | P/T |
| 1 | 184(168–195) | 200 | 237 | 176 | 129 | T |
| 3 | 203.5(190–223) | 158 | 177 | 161 | 138 | T |
| 4 | 125(116–142) | 125 | 134 | 116 | 90 | T |
| 5 | 157(n = 1) | 151 | 159 | 147 | 123 | T |
| 6 | 107.5(97–125) | 93 | 122 | 120 | 83 | T |
| 7 | 162(149–169) | 186 | 172 | 183 | 116 | P |
| 12 | 175(167–186) | 185 | 174 | 173 | 97 | P |
| 13 | 174(n = 1) | 160 | 204 | 145 | 125 | T |

TABLE IV(A)-continued

TOTAL CHOLESTEROL LEVELS BEFORE AND AFTER EACH PHASE

| | | Total Serum Cholesterol | | | | First |
|---|---|---|---|---|---|---|
| | Prestudy | Placebo(P) | | Test(T) | | Treatment |
| Subject | Average(Range) | Before | After | Before | After | P/T |
| 14 | 275(n = 1) | 247 | 240 | 242 | 196 | P |
| 15 | 143(n = 1) | 147 | 144 | 155 | 103 | P |

*n = 4 unless otherwise stated.
P = Placebo.
T = Test Formulation.

For all ten subjects, the total serum cholesterol levels observed were lower following administration of the test formulation than those observed either pre-study or post-placebo. Administration of HPMC K8515 lowered the total serum cholesterol level by an average of 25.7% (range 13.8%–43.9%). This is in contrast to the placebo phase in which changes in serum cholesterol levels ranged from +12.2% to −10% (the average change was −2.3% which is not a significant reduction).

TABLE IV(B)

TRIGLYCERIDE LEVELS BEFORE AND AFTER EACH PHASE

| | Fasting Serum Triglycerides | | | | First |
|---|---|---|---|---|---|
| | Placebo (P) | | Test (T) | | Treatment |
| Subject | Before | After | Before | After | P/T |
| 1 | 255$^H$ | 163$^H$ | 97 | 114 | T |
| 3 | 160 | 119 | 83 | 101 | T |
| 4 | 77 | 62 | 53 | 74 | T |
| 5 | 88 | 70 | 83 | 83 | T |
| 6 | 77 | 106 | 121 | 88 | T |
| 7 | 117 | 91 | 76 | 48 | P |
| 12 | 88 | 74 | 150 | 67 | P |
| 13 | 130 | 224$^H$ | 185$^H$ | 122 | T |
| 14 | 257$^H$ | 245$^H$ | 297$^H$ | 195$^H$ | P |
| 15 | 42 | 41 | 123 | 34 | P |

Referring to TABLE IV(B) above, there was an average reduction of 2.8% in serum triglyceride levels (range +72.3% to −27.6%) during the placebo phase which is not statistically significant. In the test phase, however, the average reduction of serum triglyceride levels was 20.4% (range +39.6% to −72.4%) which is significant at the 95% confidence level by paired t-test. In six of ten subjects, the triglyceride level measured after the test phase was lower than those measured either pre-study or post-placebo.

TABLE IV(C)

LDL LEVELS BEFORE AND AFTER EACH PHASE

| | Fasting Serum LDL | | | | First |
|---|---|---|---|---|---|
| | Placebo (P) | | Test (T) | | Treatment |
| Subject | Before | After | Before | After | P/T |
| 1 | 118 | 116$^H$ | 117 | 76 | T |
| 3 | 97 | 127 | 115 | 86 | T |
| 4 | 62$^L$ | 79 | 60$^L$ | 40$^L$ | T |
| 5 | 87 | 92 | 77 | 67$^L$ | T |
| 6 | 46$^L$ | 70$^L$ | 64$^L$ | 33$^L$ | T |
| 7 | 128 | 121 | 137 | 76 | P |

TABLE IV(C)-continued

LDL LEVELS BEFORE AND AFTER EACH PHASE

| | Fasting Serum LDL | | | | First |
|---|---|---|---|---|---|
| | Placebo (P) | | Test (T) | | Treatment |
| Subject | Before | After | Before | After | P/T |
| 12 | 135 | 127 | 116 | 57$^L$ | P |
| 13 | 93 | 113 | 68$^L$ | 57$^L$ | T |
| 14 | 170$^H$ | 165$^H$ | 167$^H$ | 135 | P |
| 15 | 86 | 84 | 85 | 49$^L$ | P |

Key: H = high and L = Low

Referring to TABLE IV(C), LDL levels in the placebo phase of the study rose an average of 16.2% (range +52.2% to −5.9%) during the week which is not statistically significant. In the test phase, there was a significant lowering of LDL levels an average of 32.8% (range 13%–50.9%). For all ten subjects, the LDL level after the test phase was lower than any other level recorded.

TABLE IV(D)

HDL LEVELS BEFORE AND AFTER EACH PHASE

| | Fasting Serum LDL | | | | First |
|---|---|---|---|---|---|
| | Placebo (P) | | Test (T) | | Treatment |
| Subject | Before | After | Before | After | P/T |
| 1 | 45 | 44 | 43 | 34$^L$ | T |
| 3 | 34$^L$ | 30$^L$ | 32$^L$ | 35 | T |
| 4 | 50 | 45 | 47 | 38 | T |
| 5 | 49 | 55 | 56 | 45 | T |
| 6 | 34$^L$ | 34$^L$ | 36 | 35 | T |
| 7 | 39 | 36 | 33$^L$ | 32$^L$ | P |
| 12 | 35 | 35 | 32$^L$ | 29$^L$ | P |
| 13 | 45 | 54 | 46 | 48 | T |
| 14 | 34$^L$ | 34$^L$ | 26$^L$ | 29$^L$ | P |
| 15 | 54 | 53 | 50 | 48 | P |

Key: H = High and L = Low

The results shown in TABLE IV(D) reveal no significant trends in HDL levels in either phase of the study. Ranges were +12.2% to −10% (average −2.3% change) in the placebo phase and +11.4% to −20.9% (average −5.4%) in the test phase.

The results presented above in TABLES IV(A) through IV(D) confirm that the water-soluble, high viscosity cellulose ethers of the present invention have utility in the treatment of hyperlipidemia. More particularly, coadministration of the test formulation, HPMC K8515, with a normal meal produced a dramatic effect on serum lipid levels, significantly lowering both total cholesterol and LDL cholesterol levels in all subjects studied within a one week time period. An average lowering of 26% was observed for total cholesterol and for LDL cholesterol the average lowering was 33%. Triglyceride levels were also reduced in the majority of subjects, with an average reduction of 21%. Advantageously, HDL levels were unaffected by administration of the HPMC K8515 test formulation.

C(ii). Tolerance to Use of Water-Soluble, High Viscosity Cellulose Ethers in Healthy Subjects Tolerance to the test formulation of Example 1 was assessed in a single dose study followed by a one-week block crossover study in young, healthy men. The tolerance study was conducted in a manner similar to the study on the effects of intake of the water-soluble, high viscosity cellulose ether compositions of the present invention on the serum lipid profile reported in Section C(i). above.

In one phase of the study, subjects received the test formulation with each of three meals per day. The test formulation comprised 10 g of the cellulose ether, HPMC K8515, in 500 ml of a diet gelatin formulation in accordance with Example 1. In the other phase, subjects received a placebo diet gelatin formulation.

For three days prior to each phase, subjects were instructed to desist from foods which were excessively spicy or not part of their usual diets. No alcohol, over-the-counter medications or tobacco were permitted for three days prior to, and throughout each phase, including a 72 hour post-phase bowel movement reporting period. There was a one week wash-out period between study phases.

Data for the single dose study indicated that tolerance to the test formulation was acceptable. There were no significant differences between side effects in the test and placebo phases for the single dose study nor were there changes in bowel movement frequency or consistency.

In the one week study, questionnaires regarding side effects were distributed to the test subjects for recordation at 4, 8 and 24 hours on Day 1 and Day 7 of each phase. On Days 2–6, side effects were recorded on a 24 hour basis. The side effects specifically scored were palpitation, dizziness, headache, gastrointestinal (GI) discomfort, bloating, GI cramping, flatulence and diarrhea. The side effects were scored from 0 to 6. A score of 0 indicated that the side effect was not experienced during the recording interval. A score of 1 indicated a mild transient effect lasting less than one hour. Higher scores indicated increasing severity and duration. A score of 6 indicated that the effect was severe and persistent. Bowel movement frequency and consistency was also reported and scored.

Statistical analyses of the side effect data are presented below in TABLES V(A) and V(B). The data for Days 1 and 7 were simultaneously analyzed by a SUPERANOVA analysis of variance program, which takes into account the related effects. The results are tabulated in TABLE V(A).

TABLE V(A)

STATISTICAL ANALYSIS OF DAY 1 AND DAY 7 DATA IN THE ONE WEEK TOLERANCE STUDY

| | p values | | |
|---|---|---|---|
| Symptom | test vs. placebo[1] | Day 1 vs. Day 7[2] | time of day[3] |
| palpitations | none reported | | |
| dizziness | not analyzed | | |
| headache | 0.73 | 0.052* | 0.049** |
| heartburn | 0.34 | 0.34 | 0.38 |
| GI discomfort | 0.075* | 0.06* | 0.62 |
| bloating | 0.0067** | 0.41 | 0.098* |
| GI cramps | 0.37 | 1.0 | 0.12 |
| flatulence | 0.17 | 0.017** | 0.015** |
| diarrhea | 0.18 | 0.18 | 0.13 |

*p < 0.1,
**p < .05 (where p ≥ 0.1, no significant difference; p ≤ 0.1, significant at 90% confidence interval only; and p ≤ 0.05, significant at 95% confidence interval)
[1]p values listed in Column 1 (test vs. placebo) provide a measure of the difference in adverse responses generated by administration of the test versus the placebo meals.
[2]p values in Column 2 (Day 1 vs. 7) provide a measure of the difference in adverse effects reported on day 1 versus day 7.
[3]p values in column 3 (time of day) indicate whether the adverse effects varied with time of day.

The data for Days 2–6 were separately analyzed because the data was collected less frequently (once per 24 hours) than on Days 1 and 7. The results are presented in TABLE V(B).

TABLE V(B)

STATISTICAL ANALYSIS OF DATA FOR DAYS 2–6
IN THE ONE WEEK TOLERANCE STUDY

| | p values | |
|---|---|---|
| Symptom | placebo vs. test[1] | day/effect[2] |
| headache | 0.46 | .29 |
| GI discomfort | 0.77* | .91 |
| bloating | 0.014** | .14 |
| GI cramps | 1.00 | .72 |
| flatulence | 0.098* | .64 |
| diarrhea | 0.20 | .78 |

*$p < 0.1$,
**$p < .05$ (where $p \geq 0.1$, no significant difference, $p \leq 0.1$, significant at 90% confidence interval only; and $p \leq 0.05$, significant at 95% confidence interval)
[1]p values listed in Column 1 (test vs. placebo) provide a measure of the difference in adverse responses generated by administration of the test versus the placebo meals.
[2]p values in Column 2 (day/effect) indicate whether the adverse effect varied from day to day.

In summary, the results indicate that the test formulation, at therapeutically useful dosage levels, is well tolerated in humans. Adverse responses resulting from administration of the test formulation were constrained to the GI tract, and were limited to transient mild bloating, transient gastrointestinal discomfort, and showed no trend over time. The more distressing effects which are typically attendant to ingestion of large quantities of dietary fiber, such as severe flatulence and cramping, are not induced by administration of the HPMC test formulation. Administration of the HPMC test formulation led to a modest increase in the frequency of bowel movements, but produced no change in the consistency thereof. This is in marked contrast to the constipation associated with administration of cholestyramine for control of hypercholesterolemia, for example.

Moreover, there was no change in body weight or alteration in fasting serum glucose levels as a result of administration of the test formulation. TABLES VI and VII show the fasting glucose levels and subject body weight, respectively, before and after each phase of the tolerance study. Overall, the HPMC test formulation appears to be well tolerated as compared to dietary fibers, such as oat bran or guar, that have been proposed for the treatment of diabetes and/or hypercholesterolemia.

TABLE VI

| | Glucose Level (mg %)* | | | |
|---|---|---|---|---|
| | PLACEBO | | TEST | |
| Subject | Before | After | Before | After |
| 1 | 77 | 86 | 88 | 100 |
| 3 | 94 | 87 | 86 | 91 |
| 4 | 95 | 100 | 90 | 99 |
| 5 | 94 | 92 | 91 | 96 |
| 6 | 87 | 86 | 89 | 90 |
| 7 | 91 | 91 | 98 | 88 |
| 12 | 88 | 92 | 97 | 87 |
| 13 | 70 | 89 | 84 | 85 |
| 14 | 93 | 85 | 87 | 89 |
| 15 | 98 | 88 | 92 | 85 |

TABLE VII

| | Weight (kg) | | | |
|---|---|---|---|---|
| | PLACEBO | | TEST | |
| Subject | Before | After | Before | After |
| 1 | 69.0 | 69.7 | 69.0 | 69.0 |
| 3 | 83.6 | 81.6 | 84.3 | 83.9 |
| 4 | 79.9 | 80.5 | 80.9 | 80.3 |
| 5 | 99.0 | 98.6 | 99.9 | 98.4 |
| 6 | 90.0 | 90.0 | 89.7 | 89.7 |
| 7 | 79.8 | 80.0 | 80.6 | 80.5 |
| 12 | 75.2 | 75.1 | 75.2 | 73.8 |
| 13 | 73.9 | 76.3 | 73.1 | 74.4 |
| 14 | 82.8 | 82.9 | 82.3 | 83.7 |
| 15 | 75.5 | 74.9 | 75.3 | 75.3 |

C(iii). Effects of Water-Soluble, High Viscosity Cellulose Ethers on Mildly Hypercholesterolemic Patients The ability of the water-soluble, high viscosity cellulose ether compositions of the present invention to affect the serum lipid profile of mildly hypercholesterolemic patients was investigated in an efficacy trial. "Mildly hypercholesterolemic" was defined as a total serum cholesterol level greater than or equal to 200 mg/dL with triglycerides not to exceed 300 μg/dL. Health status upon entering the study was confirmed by physical examination and a biochemical blood screen to assess kidney and liver function, as well as blood morphology.

This study was conducted on a double blind basis, with two two-week phases administered in a block crossover design, as described hereinabove in Section C(i). In one phase of the study, subjects received the test formulation (500 ml sugar-free gelatin containing 10 g HPMC K8515) with each of three meals per day. In the placebo phase, 1 tablespoon of applesauce was dispersed in 500 ml sugar-free gelatin to modify its texture, thereby reducing the ability of the subjects to discern test formulation from placebo formulation. There was a four week washout period between phases.

Questionnaires regarding side-effects were completed for the previous 24 hours on the mornings of days 2, 8, and 15 of each phase. Bowel movements (number and consistency) were recorded on days 5, 6, and 7 of each phase. Scoring criteria for side effects and bowel movement consistency was the same as reported in Sec. C(ii) hereinabove. On days 1 and 15, after an overnight fast, the following parameters were measured: weight, vital signs, serum glucose, serum lipids, biochemistry and blood morphology. Fasting serum lipids were measured on day 8 of each phase. Additionally, on day 15 of each phase, a blood sample was drawn to assess prothrombin time and ratio.

The results are reported below in Table VIII as a means ± standard deviation or (range) for all parameters measured. Lipid levels were compared between equivalent days of the placebo and test phases to determine the effects of HPMC K8515 administration on the serum lipid levels. LDL:HDL ratios were calculated from day 8 data, and the mean values are shown on the Table VIII. For all comparisons, differences were considered significant if $p \leq 0.05$.

TABLE VIII

LIPID LEVELS IN TEN SUBJECTS WITH MILDLY ELEVATED CHOLESTEROL LEVELS

| LEVEL | STUDY PHASE | | | | | | p value |
| --- | --- | --- | --- | --- | --- | --- | --- |
| | Placebo | | | Test | | | Day 15 test vs |
| mg/dl | Day 1 | Day 8 | Day 15 | Day 1 | Day 8 | Day 15 | Day 15 Placebo |
| $C_{TOT}$ | 224(19) | 221(28) | 209(21) | 223(23) | 182(29)* | 162(18)*‡ | 0.0001 |
| $C_{LDL}$ | 152(17) | 160(25) | 146(24) | 156(28) | 123(22)* | 102(21)*‡ | 0.0001 |
| $C_{HDL}$ | 46(13) | 44(12) | 43(10) | 45(12) | 41(10)* | 41(9)* | NS |
| LDL:HDL | | | 3.61 | | | 2.60 | |
| Trig. | 160(63) | 101(27)* | 124(10) | 145(44) | 109(35)* | 115(54)* | NS |

*p < 0.05 compared with Day 1 of same phase
‡p < 0.05 compared with Day 8 of same phase The data indicates that any difference in data between day 15 of the test phase and day 15 of the placebo phase are the result of ingesting the HPMC K8515. There was a 22.5% drop in total cholesterol, and a 30% drop in LDL cholesterol, and an 11% drop in HDL cholesterol. All subjects experienced a decline in total cholesterol and LDL cholesterol levels, with a significant decline being observed in each of the two weeks of the test phase. By contrast, HDL cholesterol and triglyceride levels tended to fall in the first week of the test phase and then to stabilize during the second week. There was no significant net difference in HDL cholesterol and triglyceride levels between days 15 of the placebo and test phases. Thus, the ratio of LDL:HDL cholesterol followed the LDL cholesterol pattern, with a mean drop of 28% during the test phase as compared to the placebo phase.

Side-effects and bowel movements data were analyzed by repeated measures analysis of variance using the program SUPERANOVA, which can take into account a cross-over study design. In cases where effects were significant, the pairings responsible for significance were determined by post hoc application of Tukeys test. Dizziness, GI cramping, headache and heartburn were not significantly different between the test and placebo phases. Significant adverse effects are reported below in TABLE IX.

TABLE IX

| EFFECT | PLACEBO PHASE | TEST PHASE | p VALUE |
| --- | --- | --- | --- |
| bloating | 0.40 ± 0.68 | 2.5 ± 2.13 | 0.002 |
| diarrhea | 0.23 ± 0.68 | 1.25 ± 1.55 | 0.011 |
| flatulence | 0.33 ± 0.76 | 2.6 ± 2.3 | 0.008 |
| GI discomfort | 0 | 1.33 ± 1.45 | 0.008 |

Weight, vital signs, and biochemical data were compared using a Student's paired t-test. Table X summarized the results for bowel movements, consistency and average body weight.

TABLE X

| | PLACEBO PHASE | TEST PHASE | p VALUE |
| --- | --- | --- | --- |
| Bowel Movements | 1.78 ± 0.80 | 3.2 ± 1.64 | 0.006 |
| Consistency | 2.68 | 2.64 | 0.0003 |
| Ave. Body Weight | 77.9 kg | 78.00 kg | NS* |
| Fasting Glucose | 87. mg/dL (78–79) | 85.8 mg/dL (79–94) | NS* |

*NS = not significant

Prothrombin ratios were always 1.0 or 1.1 in both placebo and test phases, likewise the prothrombin times did not differ between placebo day 15 (12.2 (11.7–12.6)) and test day 15 (12.2 (11.7–12.7)). Systolic blood pressure averaged 113.3 (106–126) at the end of the placebo phase and 120.8 (108–130) at the end of the test phase (NS). Nor were any trends observed in the diastolic blood pressure with phase.

C(iv). Dose-Response Study on Mildly Hypercholesterolemic Patients

A dose-response study was conducted on an open basis wherein twelve mildly hypercholesterolemic subjects received four levels of HPMC K8515 on an escalating basis: placebo, 10 g/day, 20 g/day, and 30 g/day. Each phase lasted one week with a minimum wash-out period of one week between phases. In the placebo phase, 1 tablespoon of applesauce was dispersed in 500 ml sugar-free gelatin. In the dose phases, the dosage amount was adjusted by changing the volume of the test formulation administered with each meal. (500 ml sugar-free gelatin containing 10 g HPMC K8515 resulted in a dosage of 30 g/day; 333 ml of the same gelatin formulation resulted in a 20 g/day dose; and 167 ml the same gelatin formulation resulted in a 10 g/day dose).

Subjects completed a questionnaire regarding adverse effects on day 7 of each phase. The number and consistency of bowel movements were recorded on days 5–7 of each phase. Weight, vital signs, and blood lipid levels were measured after an overnight fast on days 1 and 8 of each phase. Biochemical and morphological screens were drawn on day 1 of the placebo phase and day 8 of the 30 g per day phase. The data is tabulated below in Table XI.

TABLE XI

LIPID LEVELS RECORDED ON DAY 8 OF EACH OF FOUR PHASES OF A DOSE RESPONSE STUDY

| LEVEL mg/dl | p value Among Day 1 Levels | Placebo | 10G | 20G | 30G |
| --- | --- | --- | --- | --- | --- |
| $C_{TOT}$ | 0.8827 | 224(29) | 205(16) | 198(27)* | 179(25)*‡ |
| $C_{LDL}$ | 0.9119 | 161(26) | 143(17) | 136(26)* | 121(23)* |
| $C_{HDL}$ | 0.8417 | 46(14) | 43(12) | 43(12) | 40(11) |
| LDL:HDL | ND | 3.81 | 3.55 | 3.375 | 3.23 |
| Triglycerides | 0.7999 | 103(44) | 107(53) | 107(50) | 108(43) |

*p < 0.05, lower than placebo day 8
‡p < 0.05, lower than 10G day 8
ND Not Determined At a 10 g/day dosage level, there was a tendency for total and LDL cholesterol to drop between day 8 of the placebo phase and the test phase. At the 20 g/day dosage level, there was a significant decrease in both total cholesterol and LDL cholesterol, 12% and 15%, respectively. These decreases were not accompanied by a significant decrease in HDL cholesterol level. As a result, the ratio of LDL:HDL decreased by 11%. Likewise, there was a significant decrease in both total cholesterol (20%) and LDL cholesterol (25%), at the 30 g/day dose level. However, at 30 g/day, there was a tendency (not significant) for HDL cholesterol levels to fall. On the average, the LDL:HDL ratio was 15% lower after one week of following the 30 g/day regimen. Triglycerides were unaffected at all dosage levels.

Administration of the various doses of HPMC K8515 did not result in an increased level of dizziness, diarrhea, and headache between the test and placebo phases. In fact, at the 10 g/day dosage level no adverse effects were scored significantly higher than in the placebo phase. Table XII sets forth the average scores for various effects and their statistical significance. Individual pairings responsible for differences are also indicated.

TABLE XII

| LEVEL mg/dl | Placebo | 10G | 20G | 30G | p values overall treatment effect |
|---|---|---|---|---|---|
| bloating | 0.83(1.8) | 1.5(1.8) | 3.0(2.0)* | 4.0(1.7)*‡ | 0.0004 |
| flatulence | 0.5(0.7) | 2.1(1.8) | 2.8(2.0)* | 3.4(1.8)* | 0.0005 |
| GI cramps | 0.4(0.9) | 0.6(1.7) | 1.4(1.5) | 2.4(2.1)* | 0.015 |
| GI discomfort | 0.6(1.0) | 0.6(0.8) | 1.9(2.0) | 3.2(2.1)*‡ | 0.0004 |
| heartburn | 0.0 | 0.6(1.2) | 0.8(1.4) | 1.6(1.8)* | 0.0 |

*p < 0.05, lower than placebo day 8
‡p < 0.05, lower than 10G day 8

Subjects tended to lose weight during each phase of the dose-response study. The effect reached significance in the placebo phase (p<0.001) and the 20 g/day (p=0.28 and 3 g/day (p=0.0056) phases, but not in the 10 g/day phase. The average weight loss was about 1 kg, which was recovered during the wash-out period. The number of bowel movements per day was significantly higher at dosage levels of 20 g/day and 30 g/day. However, the consistency of the stools did not vary among the four phases (scores of 2.94, 2.90, 2.88 and 2.71, respectively, from placebo through 30 g/day).

In conclusion, the foregoing studies C(i) through C(iv) demonstrate that the water-soluble, high-viscosity cellulose ethers of the present invention have the ability to consistently lower total cholesterol levels by selective reduction in LDL cholesterol in both normal and mildly hyperlipidemic subjects without causing elevation of serum triglycerides.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and description in this disclosure are proffered to facilitate comprehension of the invention, and should not be construed to limit the scope thereof.

What is claimed is:

1. An ingestible pharmaceutical dosage form comprising: an active ingredient which is a water-soluble, high-viscosity grade cellulose ether having a viscosity characteristic of from about 10,000 cP (10,000 mPa·s) to about 2,000,000 cP (2,000,000 mPa·s) when in a 2 weight percent aqueous solution at 20° C., said water-soluble high-viscosity grade cellulose ether being present in an amount sufficient to effect reduction of serum lipid levels and/or attenuation of postprandial rise of blood glucose levels in an animal; and at least one pharmaceutically-acceptable inert ingredient.

2. The ingestible pharmaceutical dosage form of claim 1 wherein the cellulose ether has a viscosity range from about 25,000 cP (25,000 mPa·s) to about 800,000 cP (800,000 mPa·s).

3. The ingestible pharmaceutical dosage form of claim 2 wherein the cellulose ether has a viscosity range from about 50,000 cP (50,000 mPa·s) to about 600,000 cP (600,000 mPa·s).

4. The ingestible pharmaceutical dosage form of claim 1 wherein said water-soluble, high-viscosity grade cellulose ether is non-toxic, non-ionic, inert, and edible.

5. The ingestible pharmaceutical dosage form of claim 4 wherein said water-soluble, high-viscosity grade cellulose ether is selected from the group consisting of hydroxypropylmethylcellulose, methylcellulose and hydroxyethylcellulose.

6. The ingestible pharmaceutical dosage form of claim 5 wherein said water-soluble, high-viscosity grade cellulose ether is hydroxypropylmethylcellulose.

7. The ingestible pharmaceutical dosage form of claim 1 wherein the amount sufficient to effect reduction of serum lipid levels and/or attenuate postprandial rise of blood glucose in an animal is between about 2 grams and about 20 grams.

8. The ingestible pharmaceutical dosage form of claim 7 wherein the amount sufficient to effect reduction of serum lipid levels and/or attenuate postprandial rise of blood glucose in an animal is between about 2 grams and about 10 grams.

9. The ingestible pharmaceutical dosage form of claim 1 wherein the at least one pharmaceutically-acceptable inert ingredient is an edible food matrix.

10. The ingestible pharmaceutical dosage form of claim 9 wherein the edible food matrix is a liquid.

11. The ingestible pharmaceutical dosage form of claim 10 wherein the edible food matrix is a solid.

12. An ingestible composition for effecting reduction of serum lipid levels and/or attenuation of postprandial rise of blood glucose levels in an animal, the composition comprising:

a water-soluble, high-viscosity grade hydroxypropylmethylcellulose having a viscosity characteristic of from about 10,000 cP (10,000 mPa·s) to about 2,000,000 cP (2,000,000 mPa·s) when in a 2 weight percent aqueous solution at 20° C., said water-soluble, high-viscosity grade hydroxypropylmethylcellulose being present in an amount of from about 2 grams to about 20 grams; and a pharmaceutically-acceptable inert ingredient.

13. The ingestible composition of claim 12 wherein the pharmaceutically-acceptable inert ingredient is a food matrix.

* * * * *

UNITED STATES PATENT AND TRADEMARK OFFICE
CERTIFICATE OF CORRECTION

PATENT NO. : 5,789,393
DATED : August 4, 1998
INVENTOR(S) : Dressman, *et al.*

It is certified that error appears in the above-indentified patent and that said Letters Patent is hereby corrected as shown below:

Col. 18, line 33, change "coccurs" to -- $C_p$ occurs --;

Signed and Sealed this

Eighth Day of June, 1999

Attest:

Q. TODD DICKINSON

*Attesting Officer*   Acting Commissioner of Patents and Trademarks